United States Patent [19]
Money et al.

[11] Patent Number: 5,919,141
[45] Date of Patent: Jul. 6, 1999

[54] VITAL SIGN REMOTE MONITORING DEVICE

[75] Inventors: Eugene W. Money, Winchester; Roger Caldwell, Tullahoma, both of Tenn.; Michael Sciarra, Fairfield, Conn.

[73] Assignee: Life Sensing Instrument Company, Inc., Tullahoma, Tenn.

[21] Appl. No.: 08/748,254

[22] Filed: Sep. 13, 1996

Related U.S. Application Data

[63] Continuation-in-part of application No. 08/340,065, Nov. 15, 1994, abandoned.

[51] Int. Cl.[6] ............................................. A61B 5/00
[52] U.S. Cl. .................................... 600/513; 600/483
[58] Field of Search ............................. 600/301, 483, 600/513, 523

[56] References Cited

U.S. PATENT DOCUMENTS

| | | |
|---|---|---|
| 4,531,527 | 7/1985 | Reinhold et al. . |
| 4,784,162 | 11/1988 | Ricks et al. . |
| 4,958,645 | 9/1990 | Cadell et al. . |
| 5,012,411 | 4/1991 | Policastro et al. . |
| 5,333,617 | 8/1994 | Hafner ........................... 128/903 |
| 5,441,047 | 8/1995 | David et al. ..................... 600/301 |
| 5,544,661 | 8/1996 | Davis et al. ..................... 600/513 |
| 5,579,775 | 12/1996 | Dempsey et al. ................ 600/483 |

*Primary Examiner*—William E. Kamm
*Assistant Examiner*—George R. Evanisko
*Attorney, Agent, or Firm*—Waddey & Patterson; Mark J. Patterson

[57] ABSTRACT

A device for remote monitoring of hospitalized patient vital signs is incorporated into a portable housing, wearable by an ambulatory patient. Interfaces are provided for external connection of pulse oximetry, ECG, respiration, temperature, and blood pressure transducers. An RF transmitter transmits analog and digital vital sign data to a remote monitoring station.

2 Claims, 42 Drawing Sheets

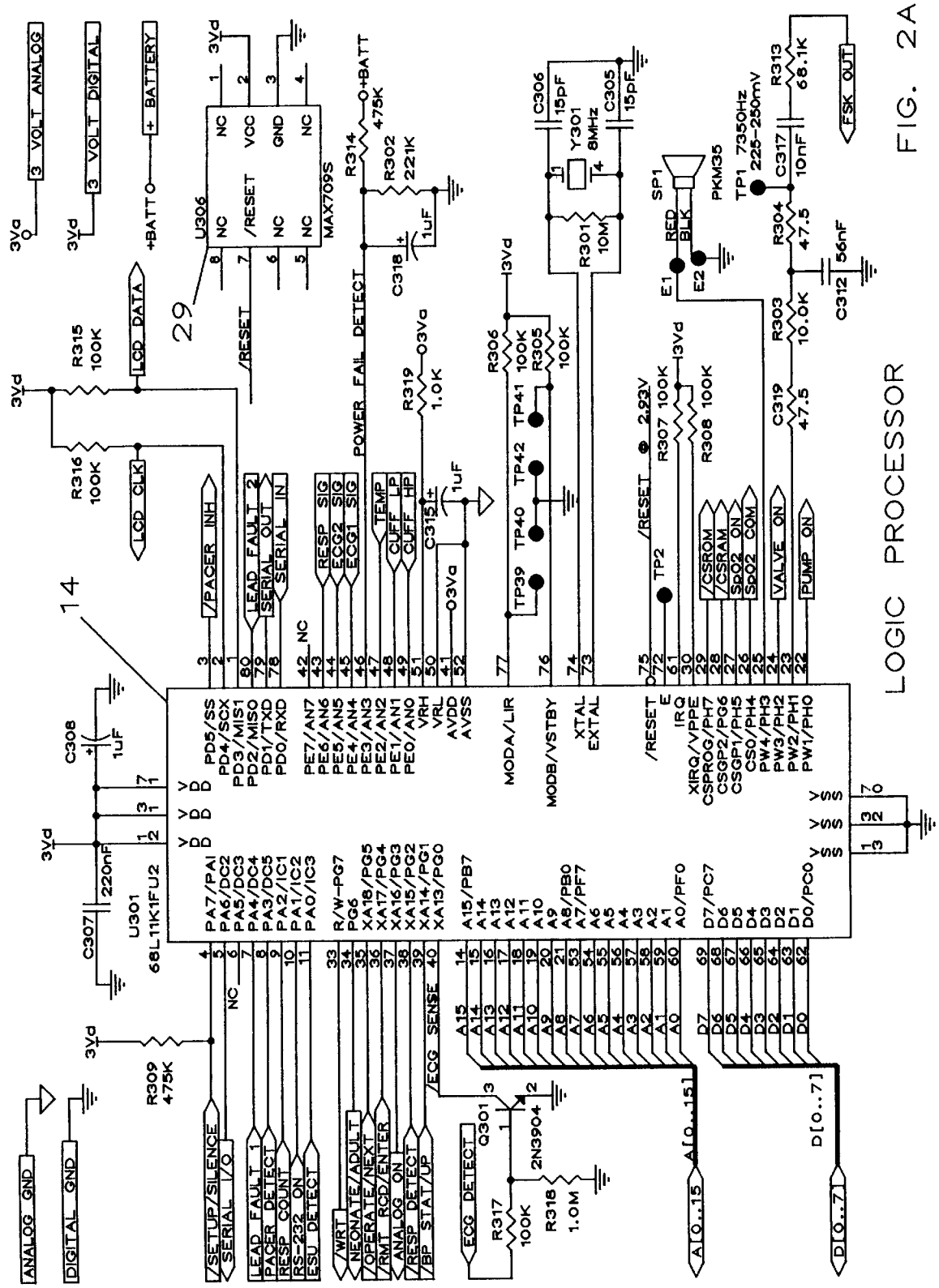

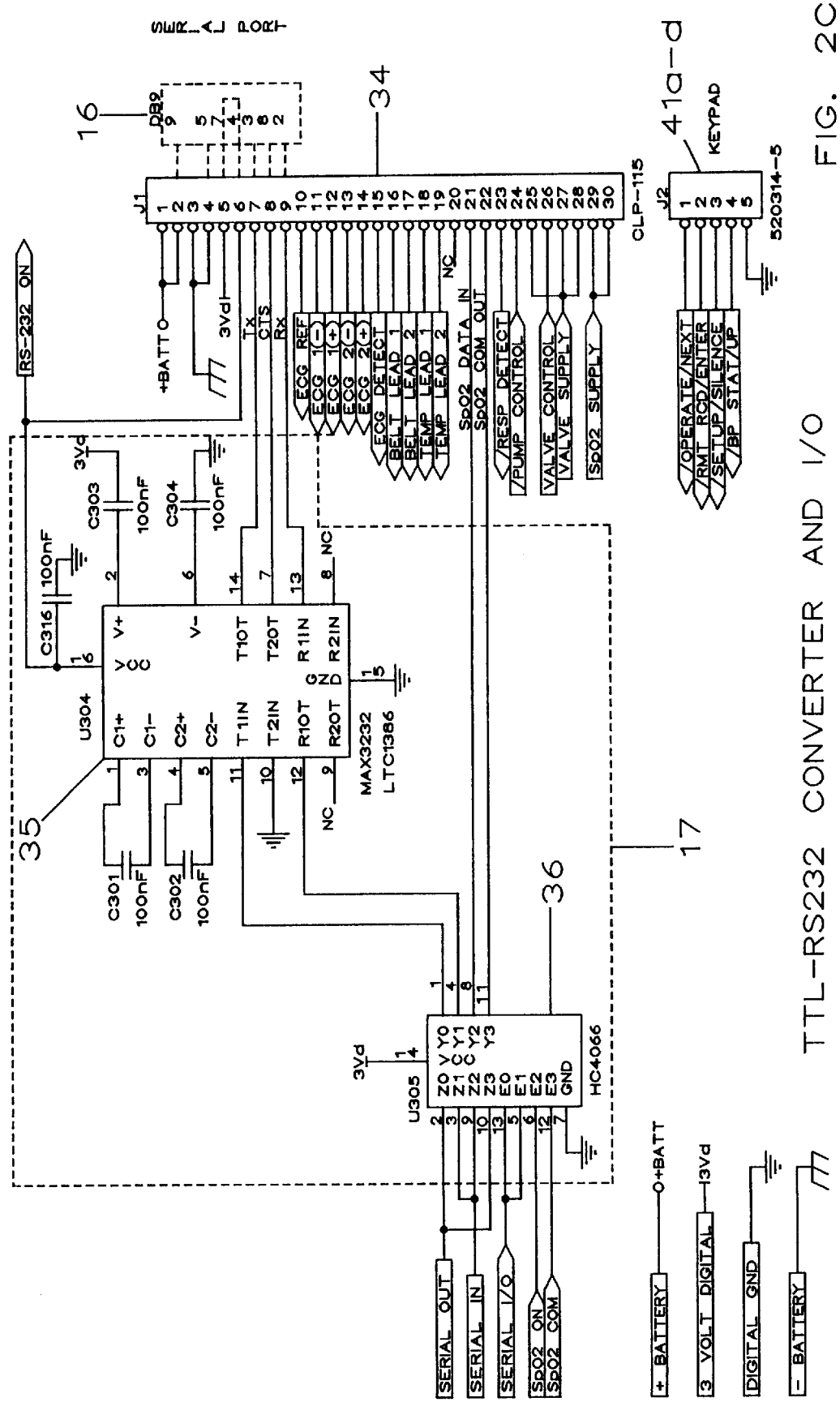

Piezo Task

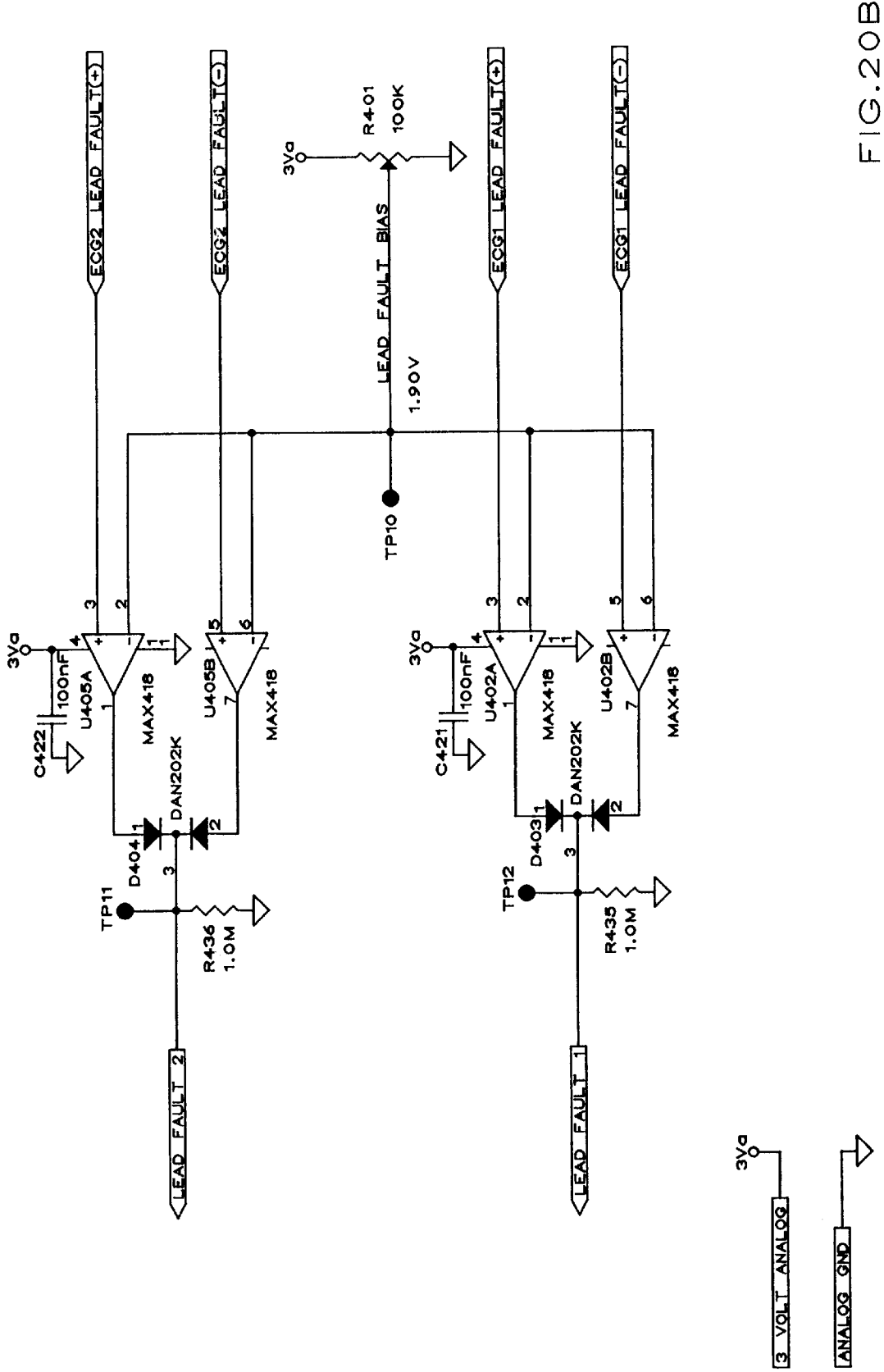

VITAL SIGN REMOTE MONITORING DEVICE

This is a continuation in part of applicant's copending U.S. patent application Ser. No. 08/340,065, filed Nov. 15, 1994, now abandoned.

BACKGROUND OF THE INVENTION

The present invention pertains to devices and systems used in hospitals to monitor vital signs associated with a hospitalized patient. More particularly, the device of the present invention is directed to portable patient vital sign monitors which can receive and process raw vital sign data from a variety of vital sign transducers associated with an ambulatory patient and transmit the processed vital sign data to a remote location.

Health care professionals are fully aware of the need to monitor, on a frequent or continuous basis, the vital signs associated with a hospitalized patient, particularly those who are seriously ill. Virtually every hospitalized patient requires periodic measurement and logging of temperature, pulse rate, and blood pressure. Many patients also need frequent determination of respiration rate, cardiac activity, and pulse oximetry. Such monitoring has typically been performed by having a health care worker periodically visit the bedside of the patient and measuring and/or observing the patient's vital signs using dedicated equipment that is either hooked up to the patient or brought into the patient's room. Such a monitoring procedure is not ideally cost effective because if all hospitalized patients are monitored in this way, it is highly labor intensive. Further, the monitoring of patients who may be ambulatory, or who may wish to be ambulatory, cannot effectively be accomplished by either continual bedside monitoring or by frequent visitation by a health care worker.

In an attempt to improve the efficiency of vital sign monitoring under these conditions, a number of devices and systems have been developed which have been only partially effective. For example, in U.S. Pat. No. 3,638,642, a monitoring system is described in which the patient wears a sensor unit capable of monitoring temperature, pulse, and a single channel ECG. The monitored information is transmitted back to the patient's room where it can be observed on a bedside monitor. However, the system of the '642 patent is deficient in that it cannot handle other patient vital signs such as non-invasive blood pressure, respiration, pulse oximetry, and multiple channel ECG. Further, it does not provide for transmission of the patient vital signs to a centralized monitoring system.

The remote ECG monitoring system of U.S. Pat. No. 3,986,498 provides a patient worn ECG sensor and transmitter device which sends signals to a receiving unit located in the patient's room, which can re-transmit the monitored signals to a central monitoring station. The system of the '498 patent, however, does not allow for simultaneous display and monitoring of other patient vital signs.

A physiological data monitoring system is described in U.S. Pat. No. 4,784,162, which includes sensors for breath sounds, respiration, left and right ECG, position indication, and patient activity. It does not allow for convenient remote monitoring of all necessary patient vital signs.

A belt worn by a patient is shown in U.S. Pat. No. 4,909,260 to provide the ability to remotely monitor and transmit ECG signals as well as respiration data. A clip-on display is further provided. However, this device is limited in its ability to monitor, display, and transmit all needed vital signs.

A fully integrated hospital network for coordinating a variety of bedside patient monitoring devices is disclosed in U.S. Pat. No. 5,319,363. The system of the '363 patent also integrates certain RF medical telemetry devices used on ambulatory patients. However, it does not show the use of a portable device which is convenient to carry, self-contained, and capable of displaying and transmitting a plurality of vital sign parameters.

The advent of miniaturization in the field of mechanics and electronics has made possible today what was unattainable as recently as five years ago. Ideas deemed revolutionary at that time are now producing an entirely new line of compact, robust, low power devices for use by the medical profession.

A person's vital signs, namely heart rate, blood pressure, blood oxygen content, body temperature and respiration, when reported in real time, are the main body parameters thought to be indicative of that person's state of wellness at any given time. The ability to provide a safe and unobtrusive method of acquiring these parameters in real time while allowing patient mobility, has been a long sought effort in the medical instrumentation profession. To date, efforts to produce such a device have been limited to those defined as stationary or battery operated, but not worn by the patient due to excessive size and/or power requirements.

What was not known by the industry was a method whereby all the above mentioned knowledge could be assembled in a manner to produce a device meeting the requirements for a real time vital signs monitor as heretofore described. For example, the use of surface mount components in conjunction with low voltage circuit design results in a vastly superior RF circuit design as opposed to the use of each technology by itself Also lacking in the prior art was a means of utilizing a single low voltage precision valve to operate as both a controlled variable bleed and a dump valve in order to facilitate the demanding blood pressure requirements necessary for accuracy when using the oscillometric noninvasive method for blood pressure.

The means to successfully design a low voltage respiration circuit which does not incorporate the impedance pneumography, thus minimizing the effects of artifact interference due to abrupt changes in chest wall resistance and the presence of unwanted electrical signals is not general knowledge. The method of incorporating a processor based algorithm to enhance a low voltage temperature circuit design as a means of obtaining high resolution temperature data is not widely known nor in general use.

None of the prior art remote patient monitoring devices combine the ability to simultaneously display and transmit to a remote location respiration, non-invasive blood pressure, temperature, dual channel ECG, and pulse oximetry. Further, no prior art devices allow for remote transmission of a plurality of patient vital signs along with the ability to use the patient monitoring device as a portable stand-alone unit. Further, prior art devices which provide for monitoring at remote locations of a plurality of patient vital signs do not also include the ability of the health care worker to start and stop recording units at the central monitoring station by transmitting a record command signal from the remote patient monitoring device. Such a device is needed.

SUMMARY OF THE INVENTION

An object of the remote patient monitoring device of the present invention is to provide the capability for simultaneous monitoring of multi-channel ECG data, heart rate, pulse, pulse oximetry, temperature, respiration, and blood pressure, in a self-contained unit that can be worn by an ambulatory hospital patient.

A further object of the present invention is to provide a remote patient monitoring device that can also be used as a stand-alone patient monitor at the patient's bedside.

Another object of the present invention is to provide in a remote patient monitoring device a means to control vital sign recording devices at a central monitoring station whereby the vital signs being reported by the monitoring device can be recorded on command.

An additional object is to incorporate in a portable ECG monitor circuitry for sensing and blocking electrostatic noise as well as pacemaker pulses.

In accordance with these and other objects that will be apparent to those skilled in the art, a remote patient monitoring device is described in which all functional circuits are mounted in a housing which is compact, portable and waterproof, and which includes a front panel liquid crystal display which simultaneously reports heart and pulse rates, respiration rate and waveform, pulse oximetry, temperature, non-invasive blood pressure, and other related vital signs. Interface circuits are included in the device to allow for easy hook-up to conventional vital sign transducers attached to or associated with the patient, including inductance pneumography units. An RF transmitter circuit is included in the device to allow for the transmission of all vital sign data to a remotely located central monitoring station. First and second channel ECG wave forms are transmitted in analog form, with other vital signs digitized and encoded using FSK modulation on an VHF FM signal.

Command keys or switches are mounted on the front panel of the device housing to allow the health care worker to send a signal to the remote monitoring station to begin recording of transmitted vital sign information. An external serial port is included to facilitate debugging of the device software and for reprogramming, including changing the intervals at which vital sign information is updated.

Efficient power conversion and utilization are key factors in determining the success of a remote patient monitor, with patient mobility and comfort being a chief concern. Accordingly, the present is intended to limit the device weight to no more than 16 ounces including batteries. It was also determined that a nominal battery life of 4 to 6 days would be required to minimize disruption of patient data input to the system. This led to the decision to use four 'AA' alkaline batteries configured for 6 volt output as the main power source. The blood pressure pump which is designed to operate at 4 to 6 volts, is powered directly from the battery supply, thus ensuring maximum energy efficient power transfer to the single largest power consumer in the device. Conversion from battery supply to 3 volts at 87 to 92% efficiency is attained by utilizing a switch mode circuit designed to operate from 3.6 to 6.5 volts. The 3.12 volt output is then fed to a linear regulator for digital noise reduction and use by the analog circuits. The same primary voltage is also regulated to 2.505 volts by another linear regulator, then doubled to 5.1 volts for use by the blood pressure valve and the pulse oximetry circuit. This method of conversion to a higher voltage is very efficient and requires fewer components than a typical step up converter. The use of new technology 'high side' electronic switches which exhibit very low 'on' resistance, to control the motor and valve activation sequences is vital to maintaining adequate power when batteries are near their end of life.

DESCRIPTION OF THE PREFERRED EMBODIMENT

Hardware Overview

Figure 1:
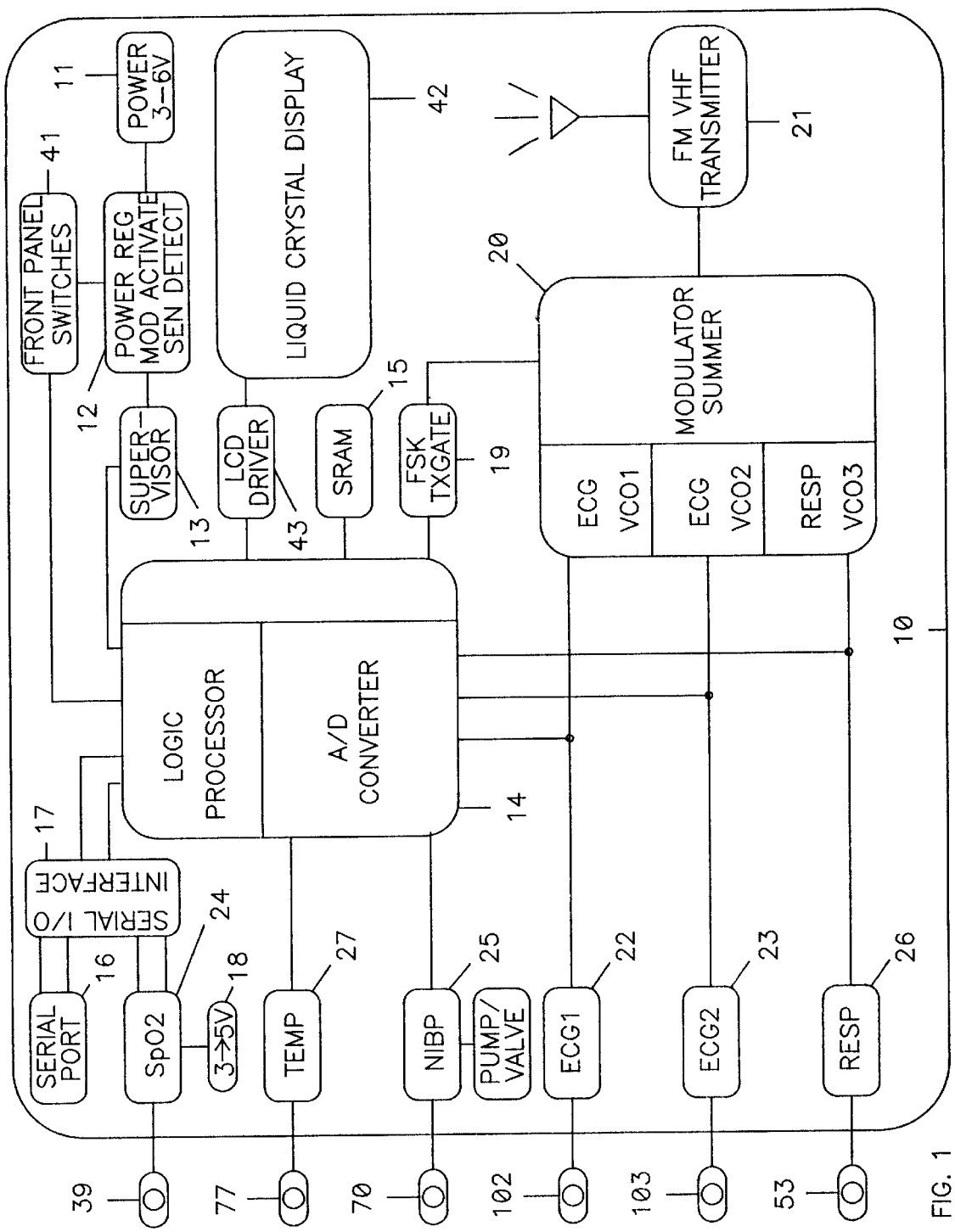
FIG. 1 is a block diagram of the various functional units and circuits of the remote monitoring device of the present invention.

The remote patient monitoring device, designated at 10 on FIG. 1, is a self-contained, portable and patient-wearable unit, with all hardware and software mounted in a housing approximately one inch thick, three inches wide, and six inches long. The housing 5 has a front panel 40 (FIG. 10) having a liquid crystal display 42 and four front panel switches 41*a–d*. Device 10 is preferably adapted for use as both a stand-alone patient vital sign monitor and for wireless transmission of vital sign data to a central monitoring station.

Figure 17A:
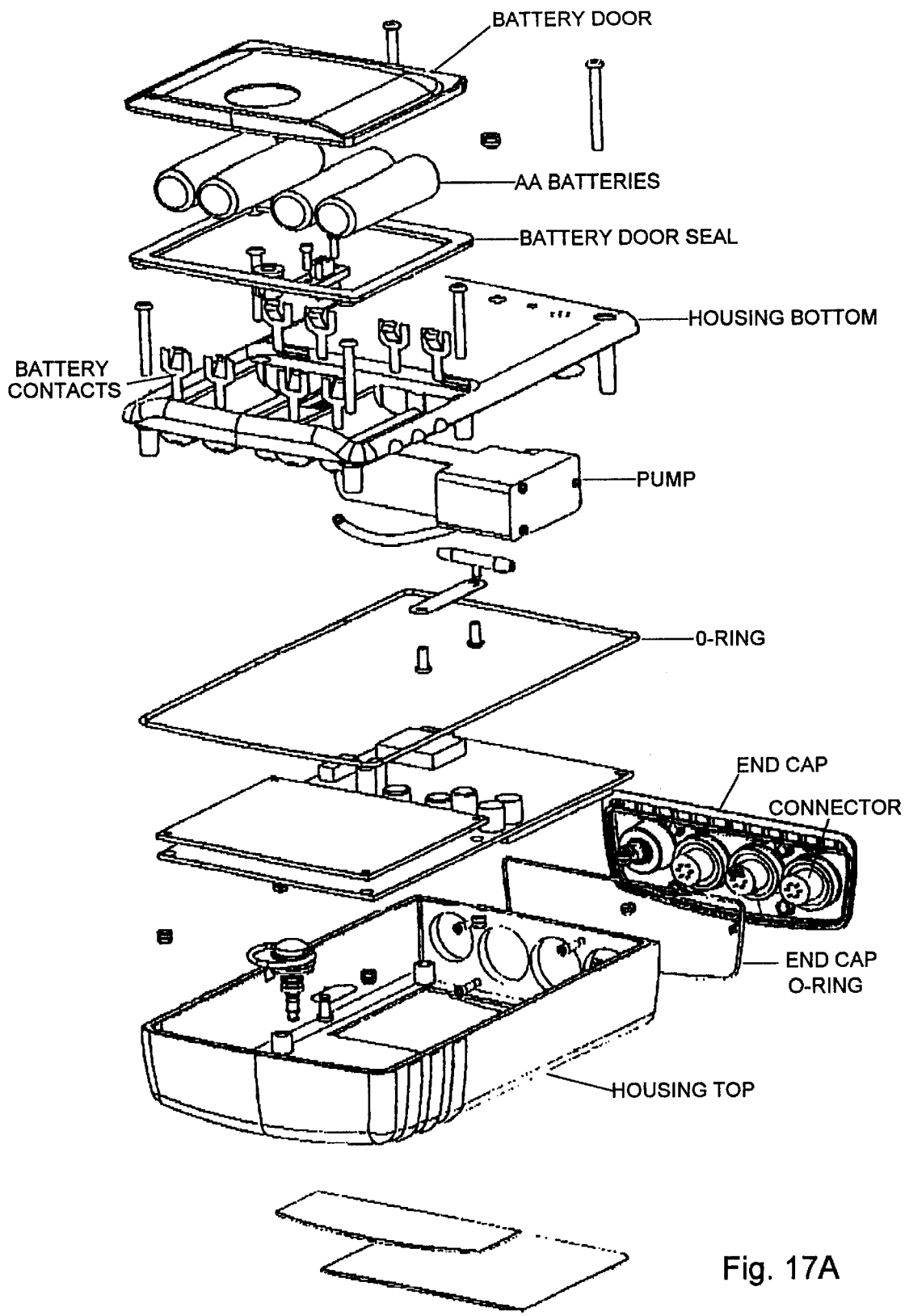
FIGS. 17a and 17b are exploded top and bottom perspective views of the housing and associated mechanical components of the remote patient monitor.
Figure 17B:
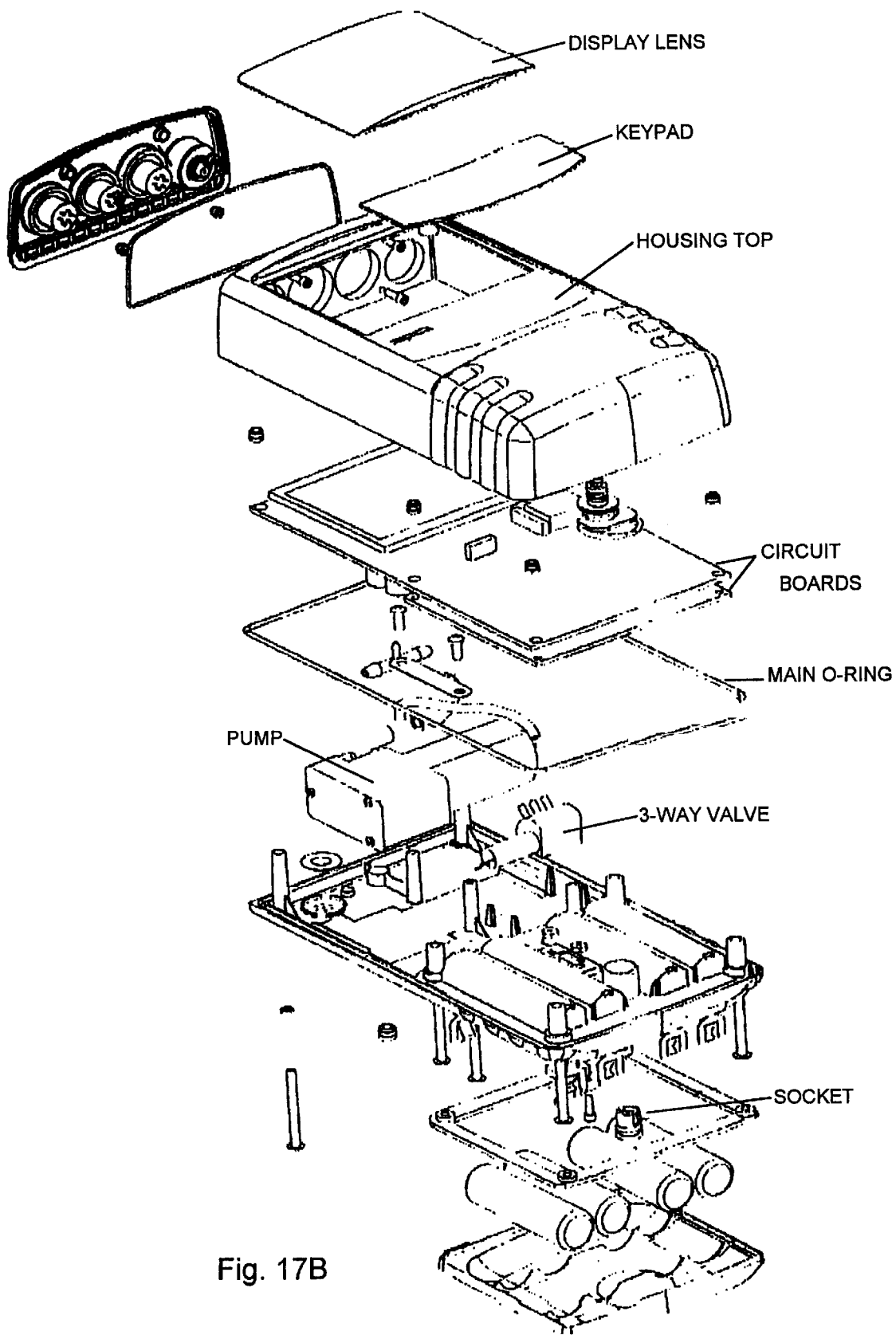

FIGS. 17*a* and 17*b* provide further detail about the housing 5 and associated mechanical parts of the device 10 including the use of seals and o-rings to provide a waterproof enclosure.

FIG. 1 illustrates in block diagram form the functional units or circuits of a preferred embodiment of the device 10. Most of the control, data processing, and data reporting functions of device 10 are controlled by a processor unit 14 which is operatively linked to a number of different functional hardware units and circuits. For maximum versatility, a preferred embodiment of device 10 will incorporate the ability to sense, process, report, and transmit two ECG channels, heart rate, pulse rate, pulse oximetry data, non-invasive blood pressure, respiratory rate and waveform, and temperature. Accordingly, first and second channel ECG interface circuits 22 and 23 are provided to receive two bipolar leads each from first and second channel ECG transducers 102 and 103. Additional noise detector and pacemaker pulse detection circuitry (FIG. 7) associated with ECG interface circuits 22 and 23, and processor 14, provide an ability within device 10 to detect the presence of electrostatic noise and/or a pacemaker pulse and to prevent that pulse and noise from distorting the accuracy of the ECG wave forms reported by device 10.

Pulse oximeter interface circuit 24 receives raw data from a conventional pulse oximeter cuff transducer 39. A separate voltage converter 18 is used to deliver regulated DC power to pulse oximeter interface circuit 24.

Non-invasive blood pressure data is received from a blood pressure cuff transducer 70 by blood pressure interface circuit 25.

The patient's respiration rate is preferably monitored by an inductance pneumography respiration belt transducer 53 which provides raw respiration data to device 10 through respiration interface circuit 26. Finally, a conventional electronic temperature probe transducer 77 provides analog temperature data to device 10 through temperature interface circuit 27.

Power to device 10 originates from four AA batteries (not shown), controlled, conditioned, and regulated by power supply circuit 11 and by a portion of power regulation and logic circuit 12. A separate processor supervisor unit 13 assists processor 14 in handling power failure detection and power fail reset functions for device 10. Data that is used by processor 14 during the carrying out of its various functions is stored in data memory unit 15, preferably a static random access memory device of conventional design.

The processed patient vital sign measurements (first and second channel ECG rate and waveform, pulse oximetry, pulse rate, heart rate, non-invasive blood pressure, respiration rate and waveform, and temperature) are reported by device 10 in two modes. First, the data (excluding ECG and respiration wave forms) is digitized using frequency shift keying (FSK) modulation and continuously displayed on an LCD display unit 42 (FIG. 10), which is driven by data outputted from processor 14 through LCD driver 43. This data is also provided for remote transmission to RF transmitter 21, through FSK data transmission gate 19 and modulation circuit 20. In addition, first and second channel ECG and respiration analog wave form data are transmitted in analog fashion, and summed with the digitized FSK vital sign data, in modulation circuit 20. The combined analog and digitized data is transmitted by RF transmitter circuit 21 on an FM RF carrier.

To provide additional versatility, serial debug and programming port 16 is provided to allow the user of device 10 to handle occasional software and hardware issues, as well as update the software which controls processor 14. Accordingly, a serial data I/O interface unit 17 is provided in device 10 to allow the user to use the serial communications interface (SCI) port on processor 14 to communicate with an external terminal for either debugging and programming purposes, or to receive data from pulse oximetry cuff transducer 39.

Display Unit

A preferred embodiment of the remote patient monitoring device 10 will be capable of fully self-contained operation as an active monitor of patient vital signs. Accordingly, looking at FIGS. 9 and 10, a rectangular flat panel liquid crystal display (LCD) 42 is incorporated into the front panel 40 of device housing 5. Display 42 is capable of simultaneous visual presentation of the following data: heart rate in beats per minute; pulse rate in beats per minute; non-invasive blood pressure, systolic and diastolic, in mm HG; respiration in breaths per minute; temperature in degrees Fahrenheit or Centigrade; pulse oximetry (SPO2) in saturation %;, and patient ID number. The patient ID number is unique to the patient monitored for tracking the patient information. The number of paced heart beats, as a percentage of total, can optionally be displayed or reserved only for remote transmission.

Figure 9:
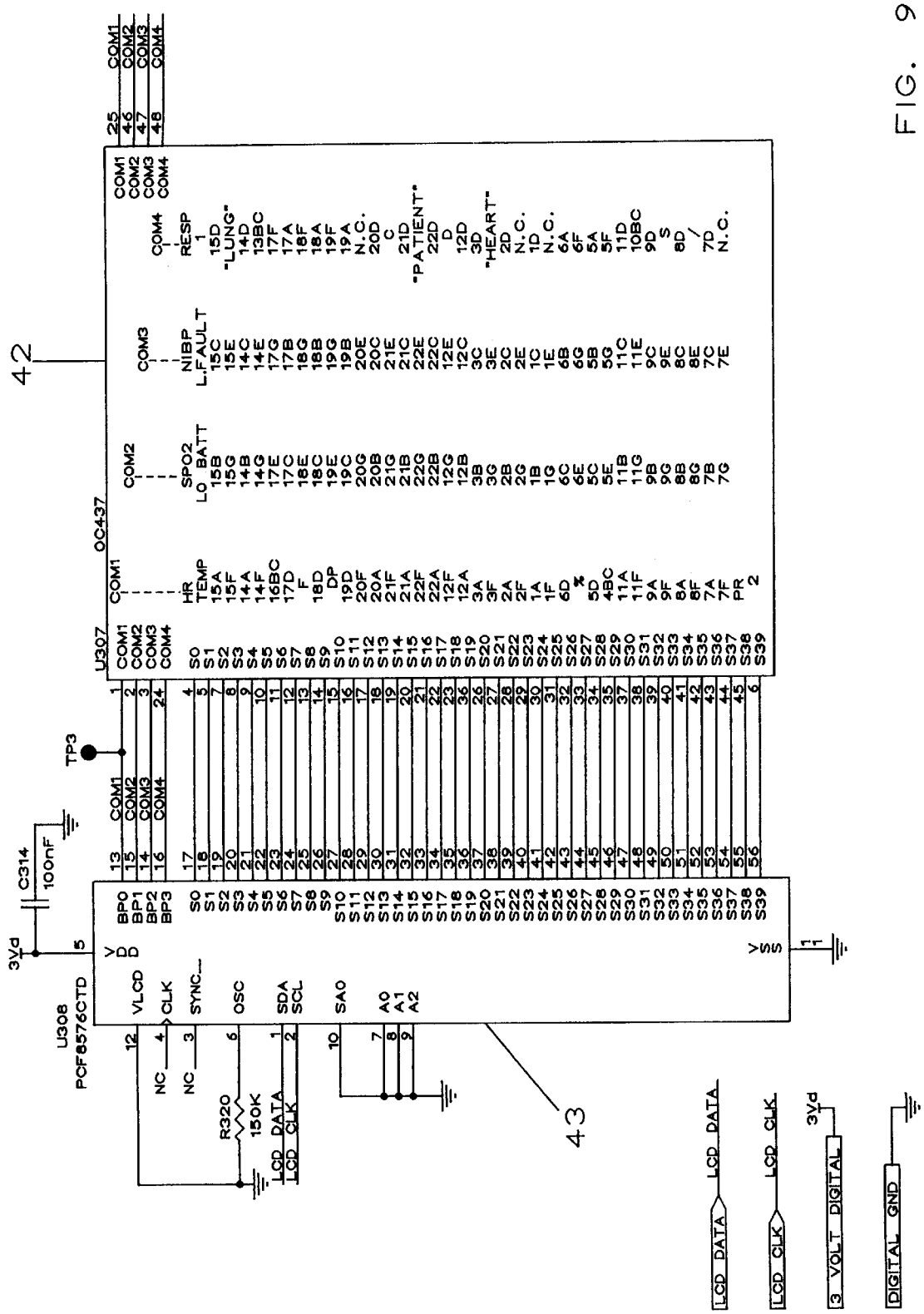
FIG. 9 is a schematic diagram of the LCD display circuit of the remote patient monitoring device.

FIG. 9 schematically illustrates the display circuitry of device 10, including LCD display 42 and associated display driver 43. In addition to vital sign data display, display driver 43 should be programmed in conjunction with processor 14 to provide visualization of certain alarm or unusual status conditions, including low battery, check SPO2, sensor/transducer lead fault, check NIBP, and check TEMP. Further, display 42 will also visually indicate that the central monitoring station is remotely recording vital sign data or that the cuff on the non-invasive blood pressure unit 70 (FIG. 1) is active.

Figure 10:
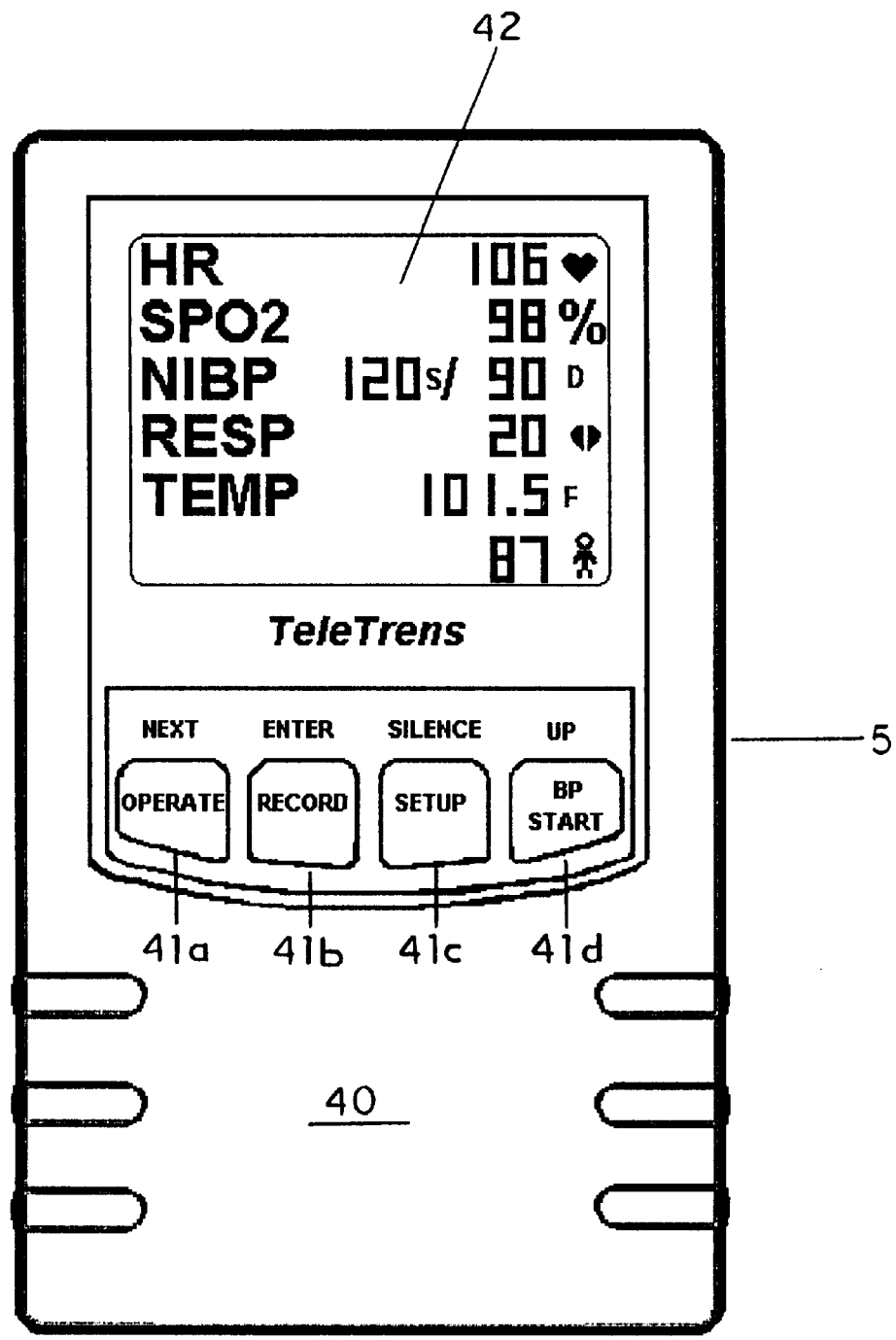
FIG. 10 is a front view of the housing of the remote patient monitoring device showing the display and front panel switches.

As seen on FIG. 10, display 42 can also have a "heart" icon which flashes in synchronization with digital pulses generated by first channel ECG interface circuit 22. During bleed down of blood pressure cuff transducer 70, the heart icon flashes when pulses from transducer 70 are detected.

Figure 6:
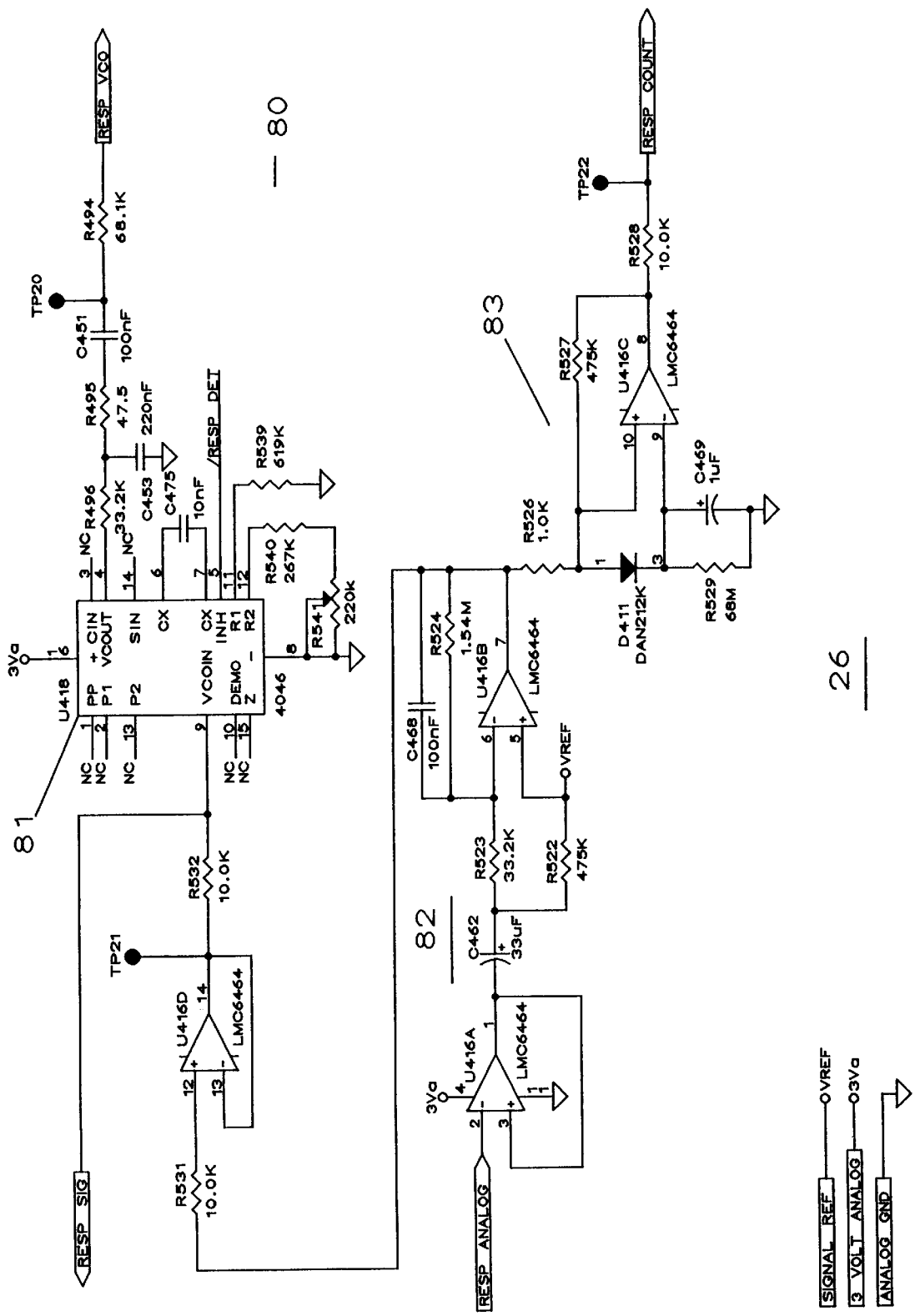
FIG. 6 is a schematic diagram of the respiration detector circuit of the remote patient monitoring device.

A "lung" icon flashes with incoming digital pulses from respiration detector circuit 80 (FIG. 6).

The TEMP, RESP and heart icons and values are displayed when the corresponding transducers are detected as being connected to device 10.

If a pulse oximeter cuff transducer 39 is detected and good data is being received, the SPO2 icon and % value is displayed.

If good data is supplied by cuff transducer 70, the NIBP, D and S icons are displayed, along with their respective values.

The Model PCF-8576T integrated circuit LCD driver from Phillips Electronics can be used in this application for driver 43. The data to be displayed (LCD DATA on FIG. 9)

and the timing signals (LCD CLK) used by driver 43 are supplied by corresponding outputs on processor 14.

Power Supply and Conditioning Circuit

Because device 10 must provide an electronic interface to a wide variety of vital sign transducers, and process both analog and digital data, it must have the capability of taking a raw 6.0 V battery voltage and supply both regulated 3.0 volts and 5 volts. Accordingly, additional detail about power supply 11 and power conditioning and logic control units 12 is illustrated on FIGS. 2, 5, and 7. Looking first at FIG. 2, power to device 10 is initially controlled by a solid state on/off switch unit 33 which is activated by operate/standby switch 41a on front panel 40 (FIG. 10) of device 10. When device 10 is turned on, raw battery power is initially supplied to switch mode power supply unit 31 which converts the raw 6 volt battery voltage to 3.4 volts. A 3.0 volt regulator 32a is used to supply regulated 3 volt power to those analog circuits and components of device 10 which require it. Similarly, regulator 32d supplies 3 volt power to the digital circuits. In addition, so that voltage regulator 30 can supply 5 volt power to pulse oximeter cuff transducer 39, a voltage doubler 18 is also connected to the output of power supply unit 31.

Additional voltage regulation is provided for blood pressure interface circuit 25 (FIG. 5) which includes 3 volt regulator 71. Similarly, pacemaker and noise detector circuit 62, shown in FIG. 7, has its own 3 volt regulator 60.

Figure 18A:
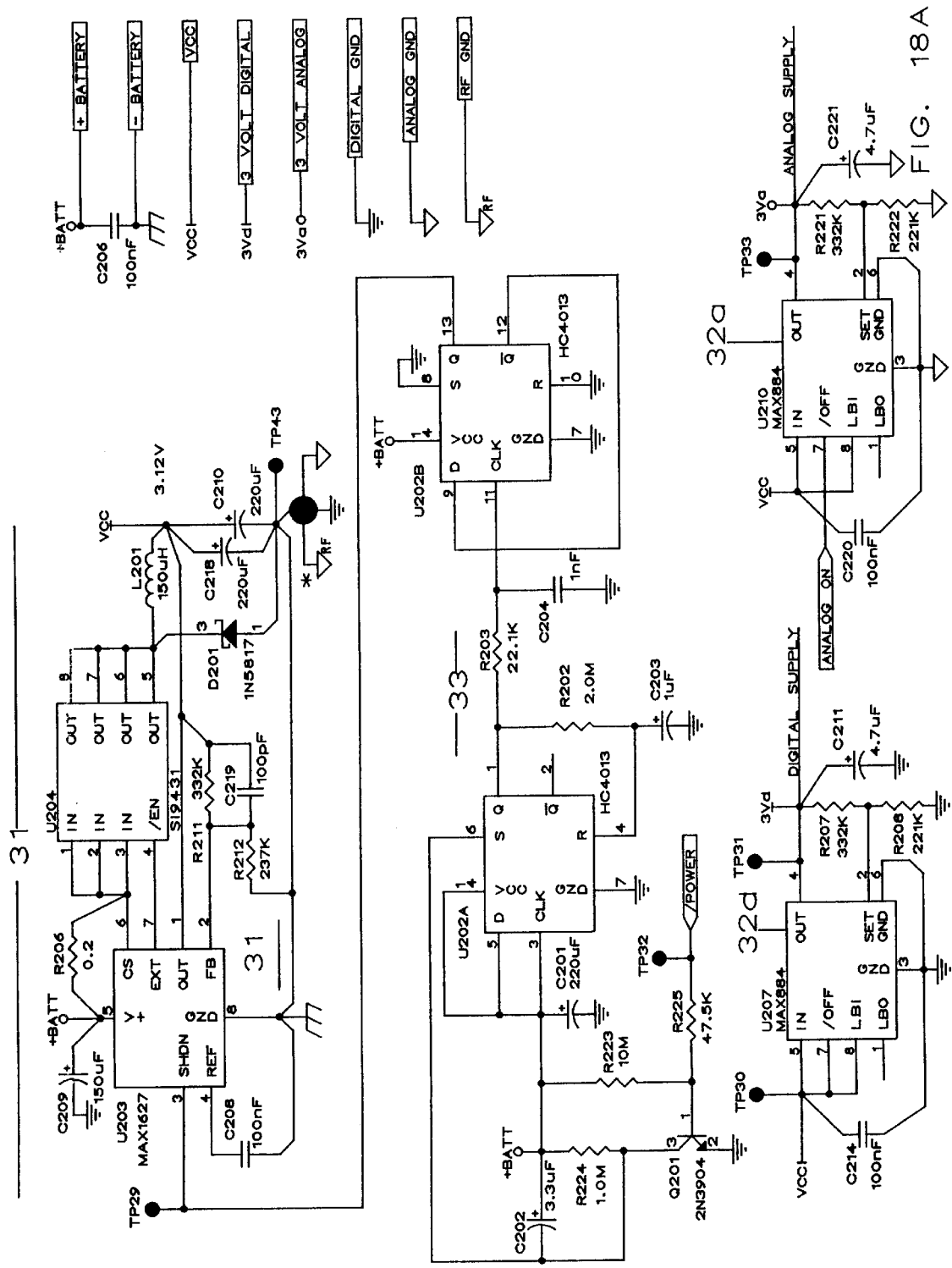
FIG. 18 is a schematic diagram of a second embodiment of the main power supply circuits of the remote monitoring device.
Figure 18B:
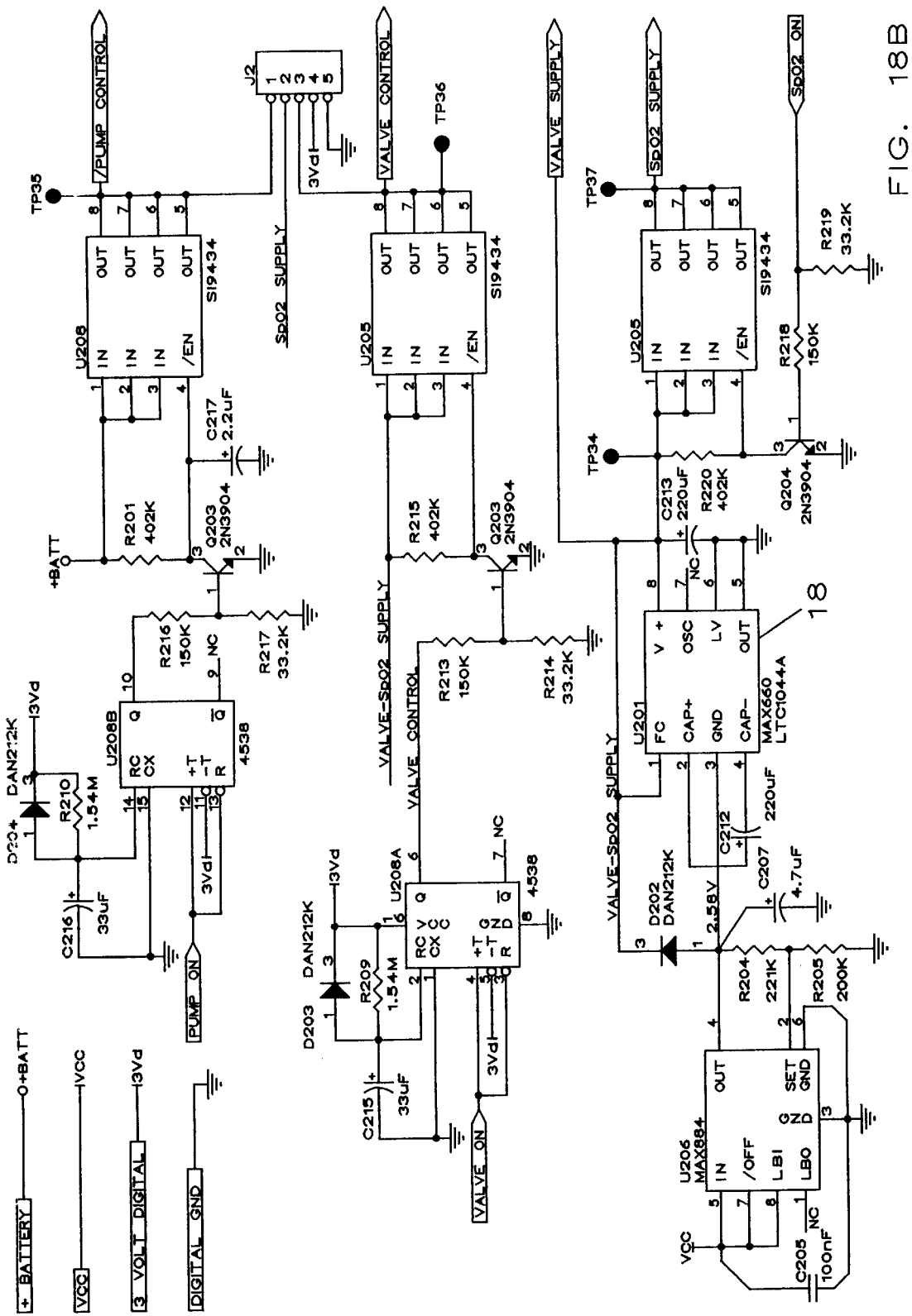
Figure 19A:
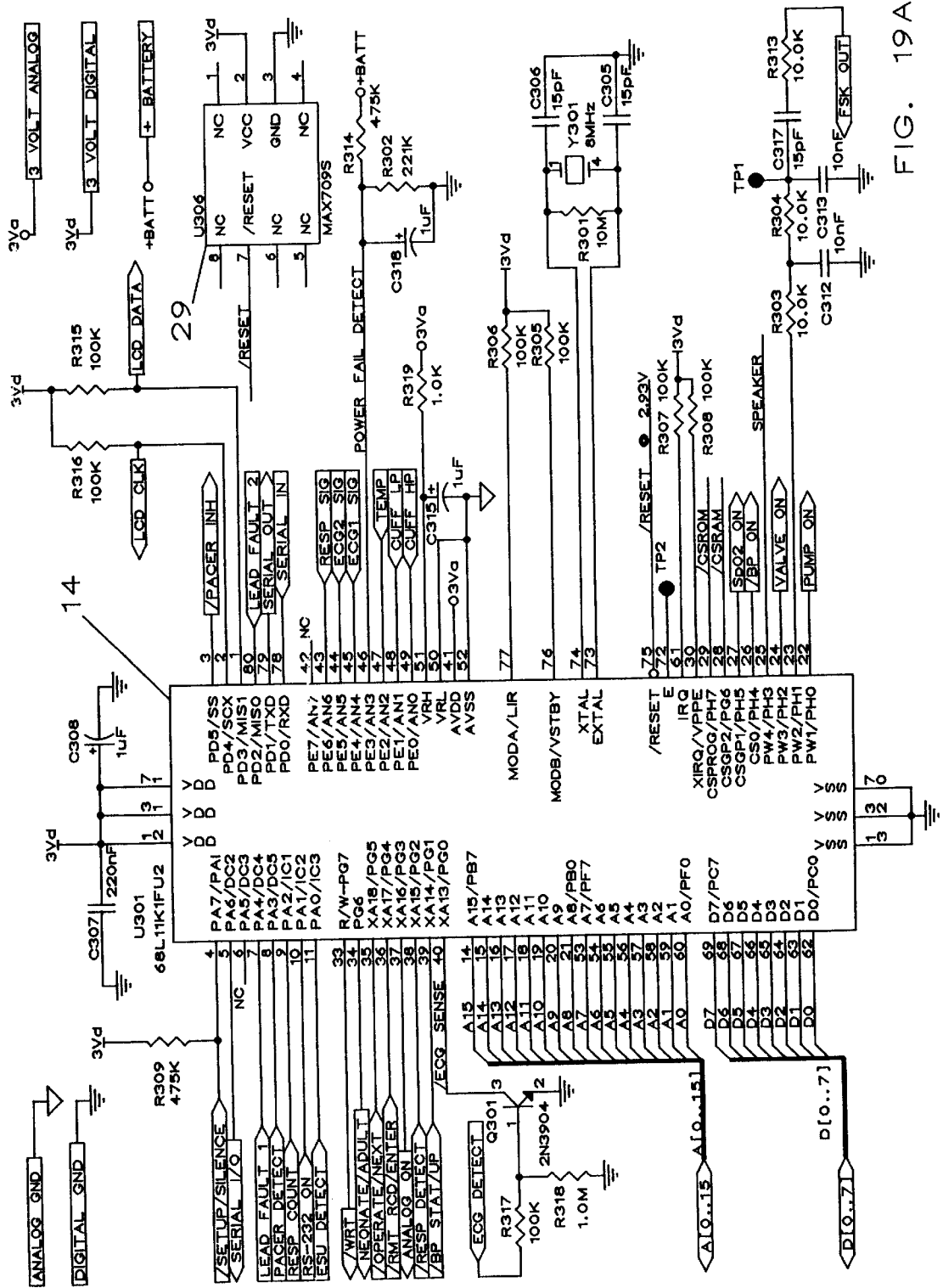
FIG. 19 is a schematic diagram of a second embodiment of the main logic circuit of the remote monitoring device.
Figure 19B:
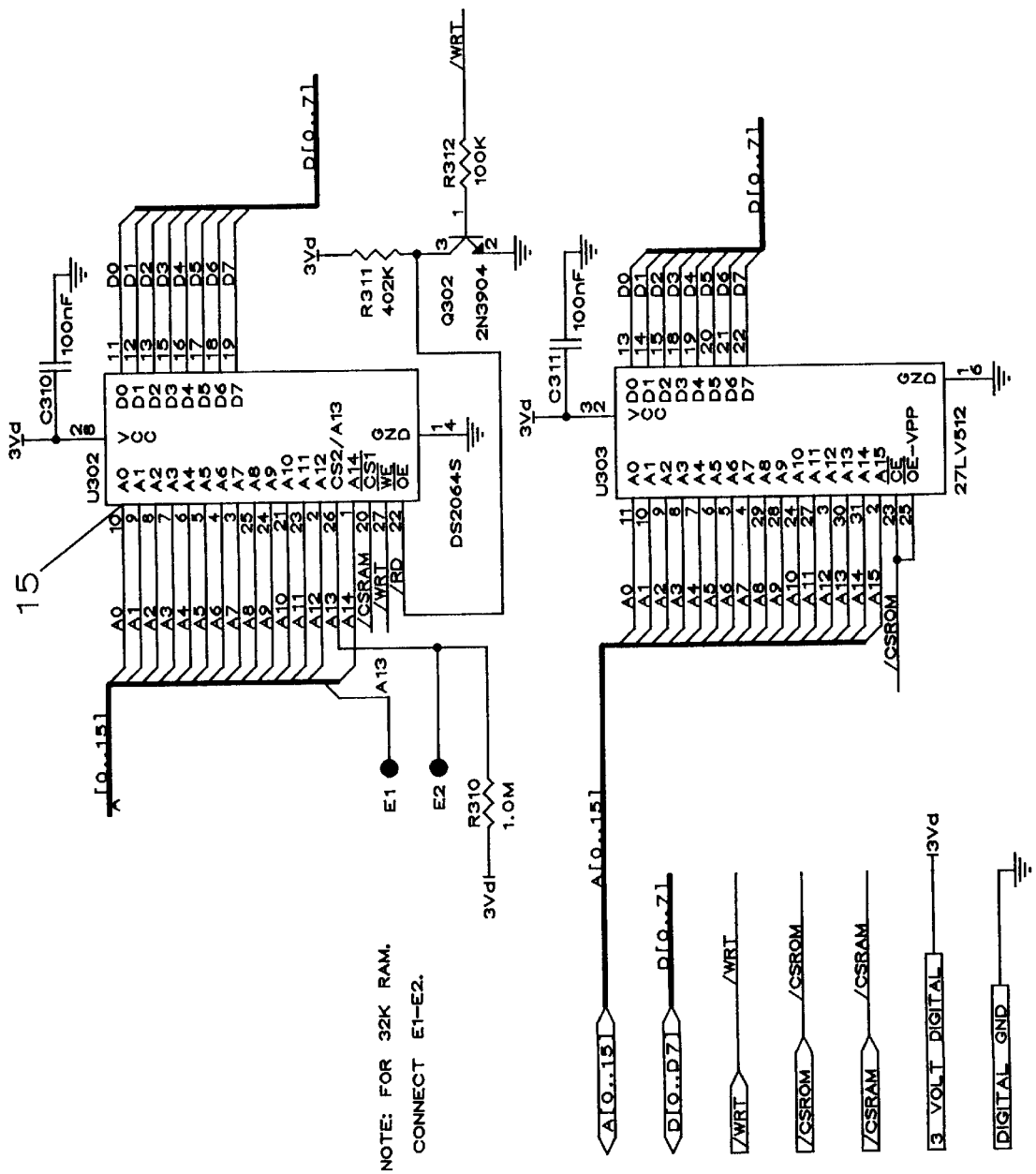
Figure 19C:
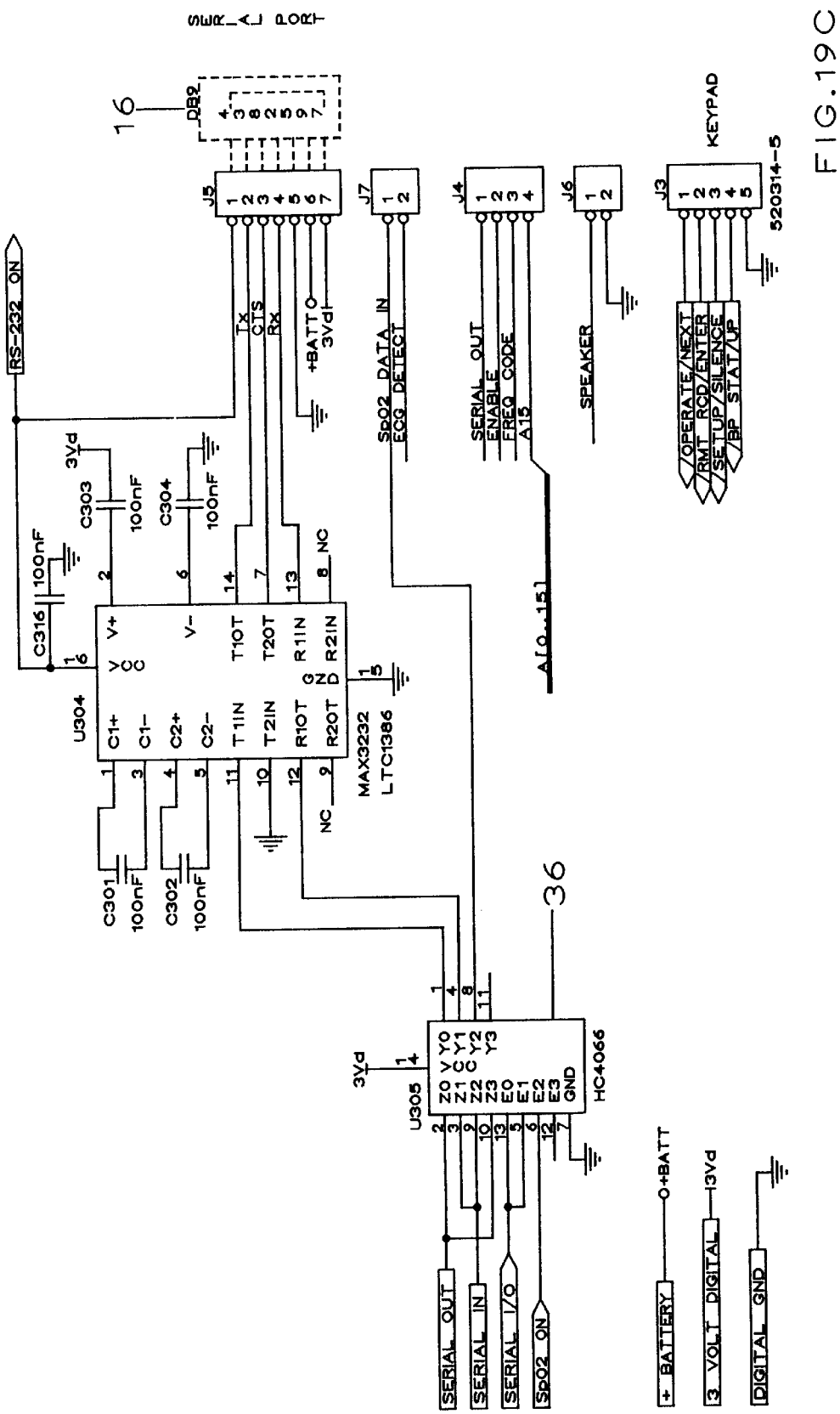
Figure 20A:
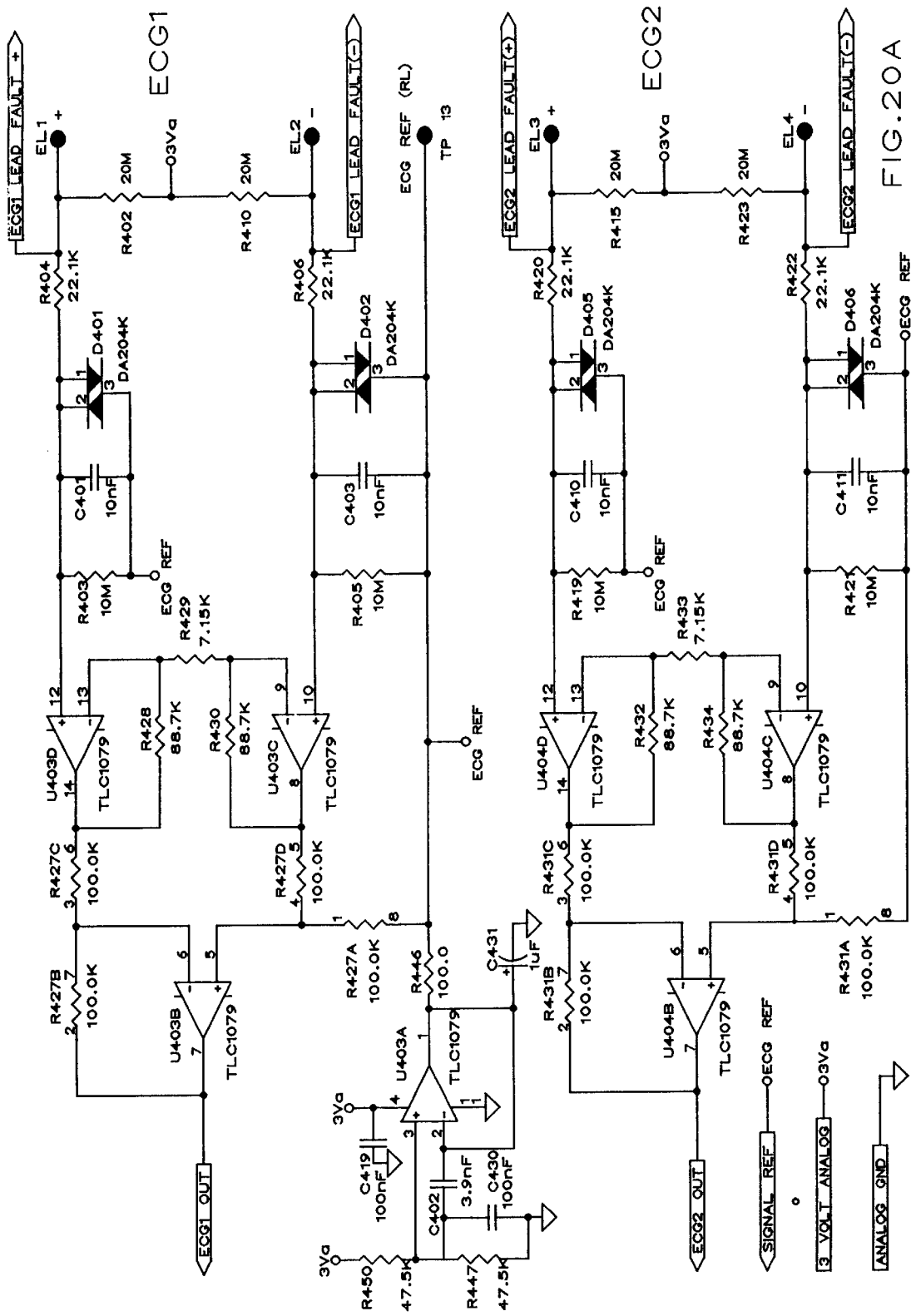
FIG. 20 is a schematic diagram of a second embodiment of the first and second channel ECG interface and VCO circuits of the remote patient monitoring device.
Figure 20C:
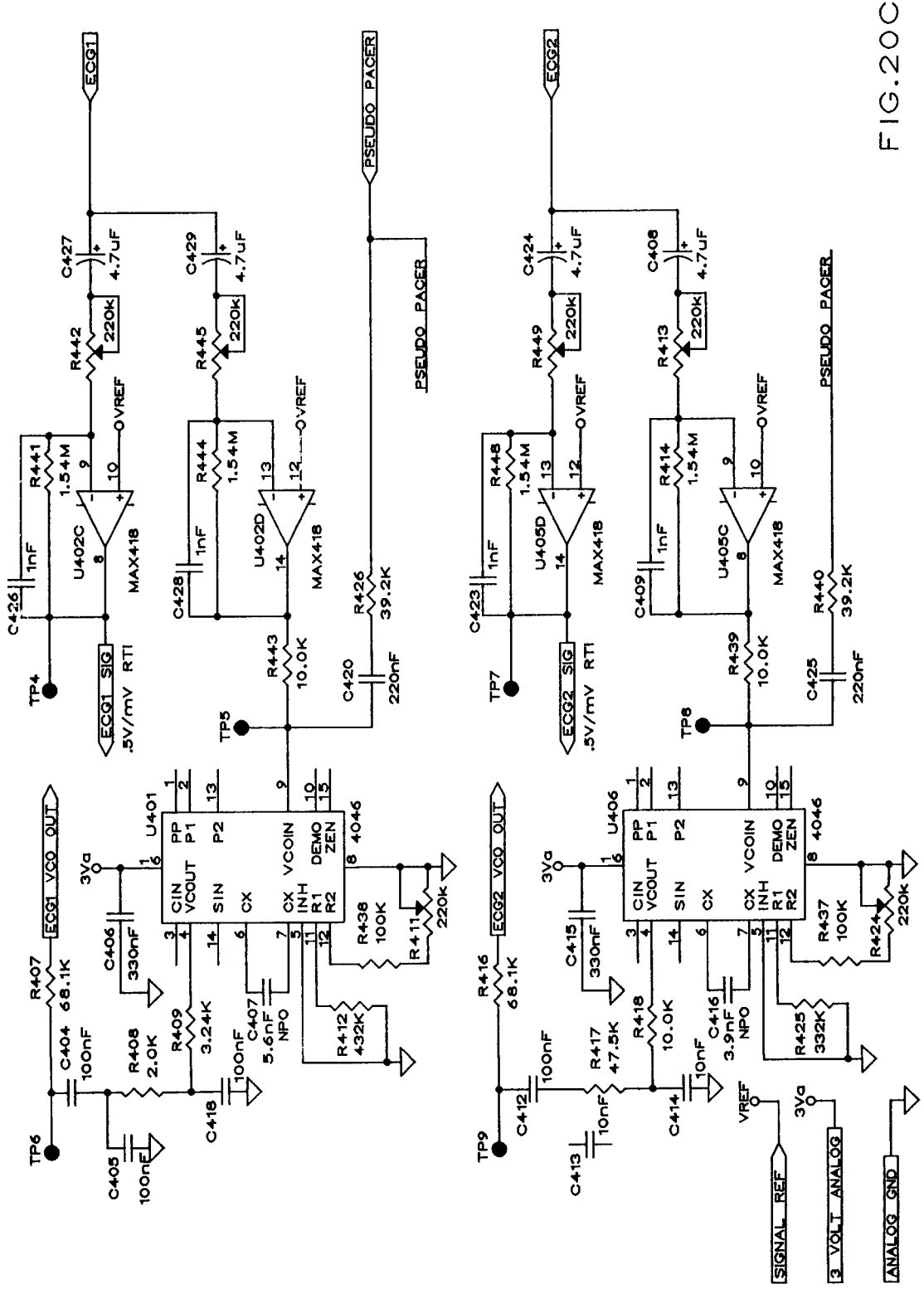
Figure 21A:
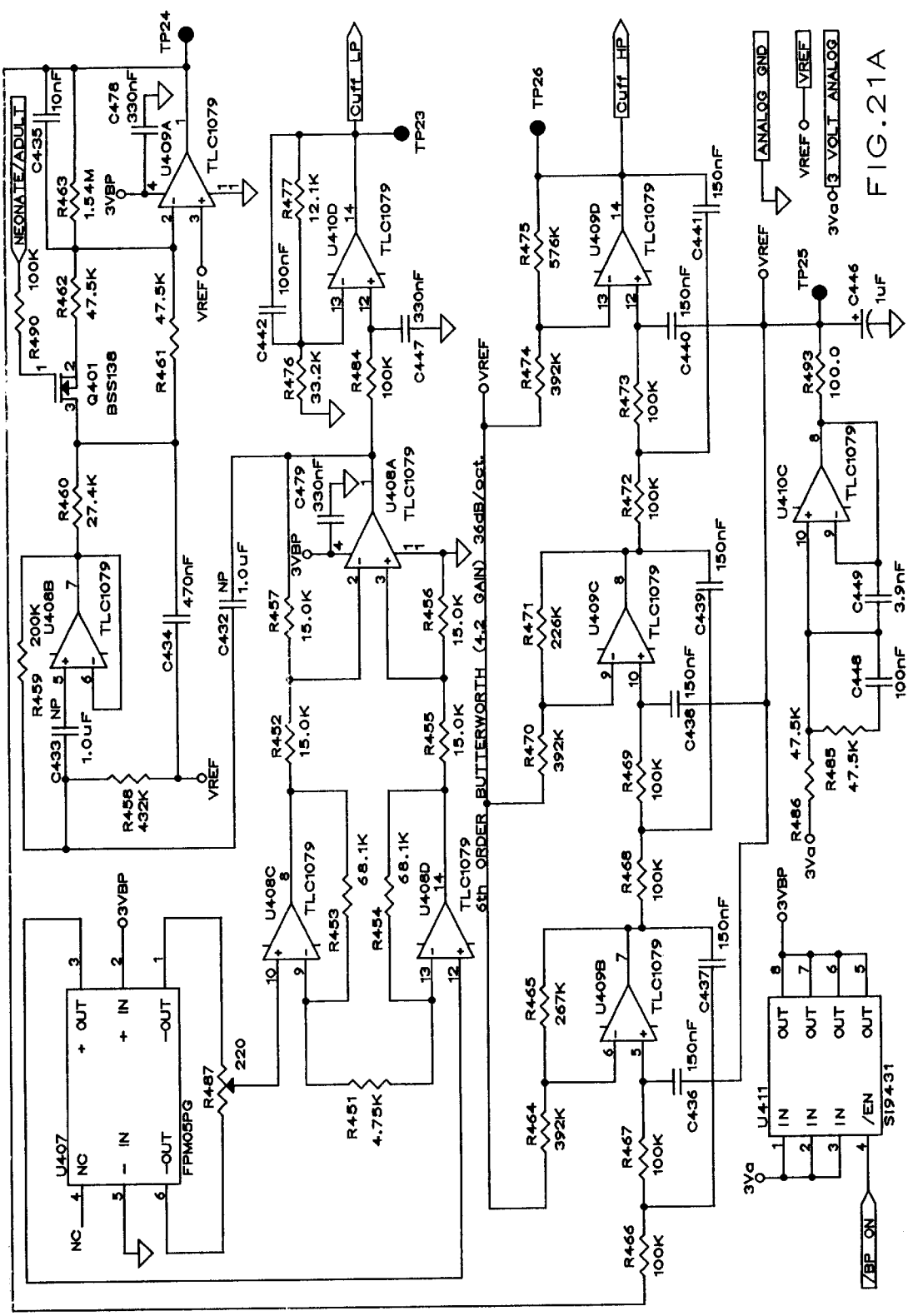
FIG. 21 is a schematic diagram of a second embodiment of the blood pressure and temperature interface circuits of the remote patient monitoring device.
Figure 21B:
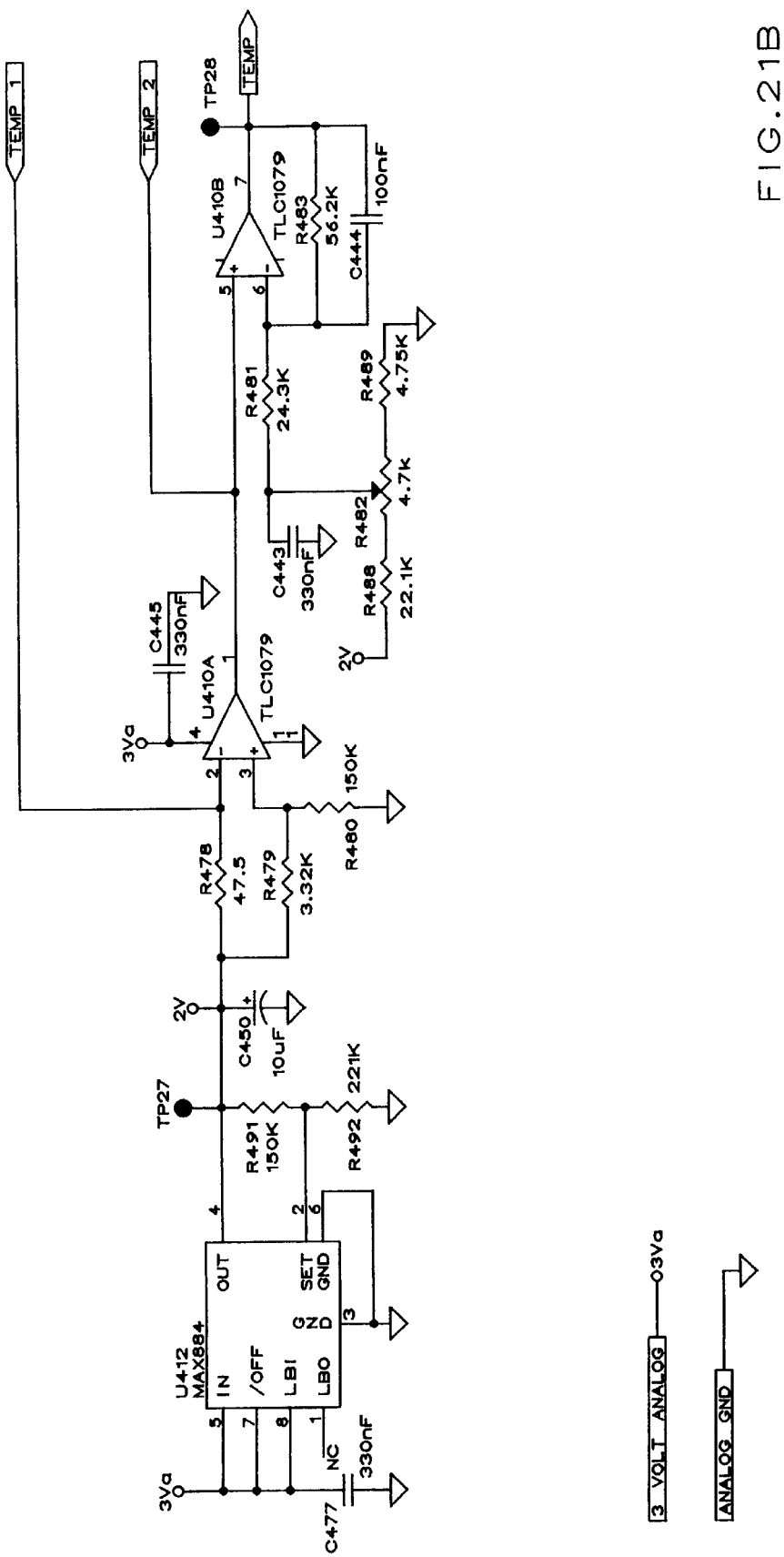
Figure 22A:
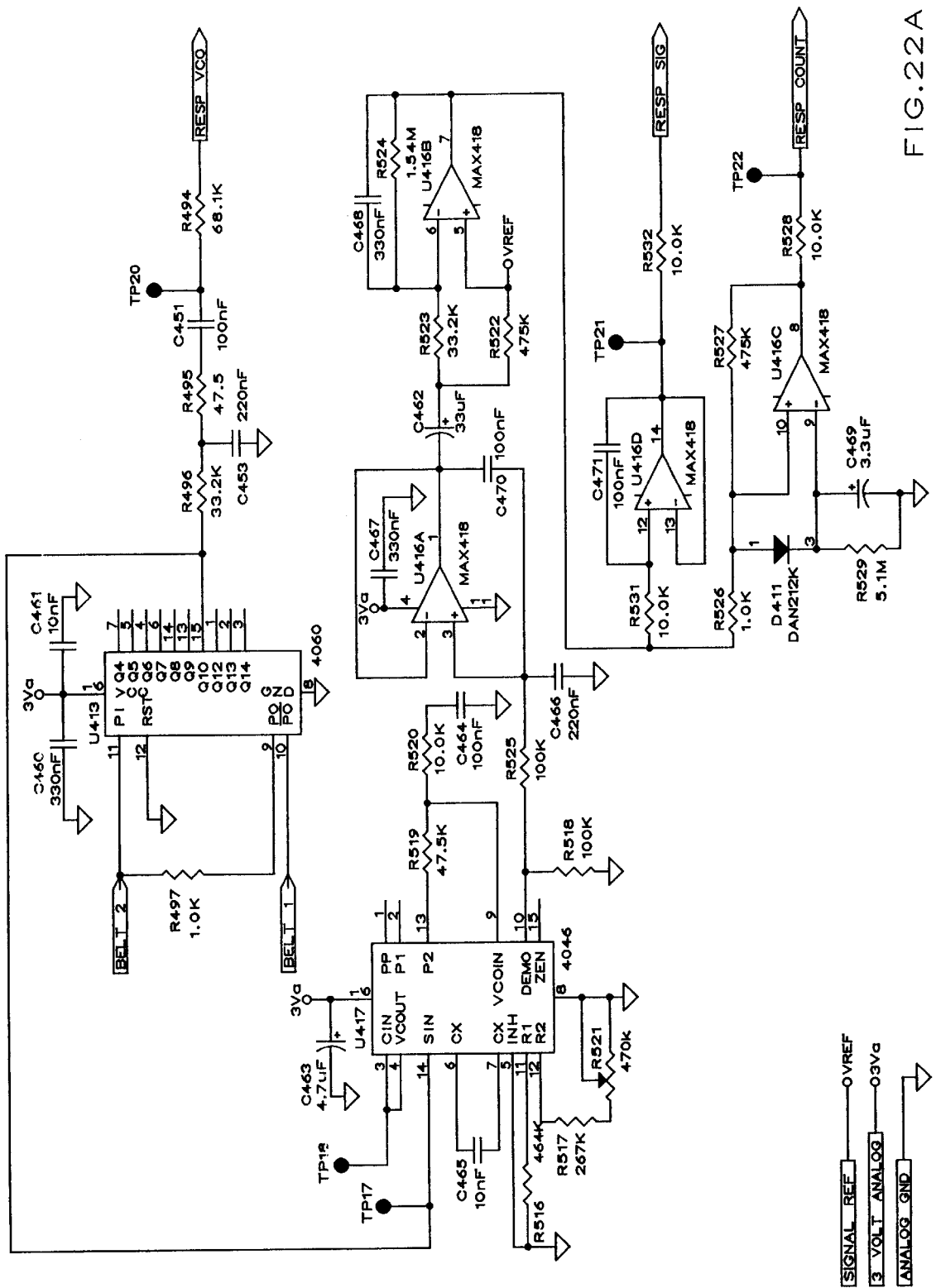
FIG. 22 is a schematic diagram of a second embodiment the respiration detector, pacemaker pulse, and noise detector circuits of the remote patient monitoring device.
Figure 22B:
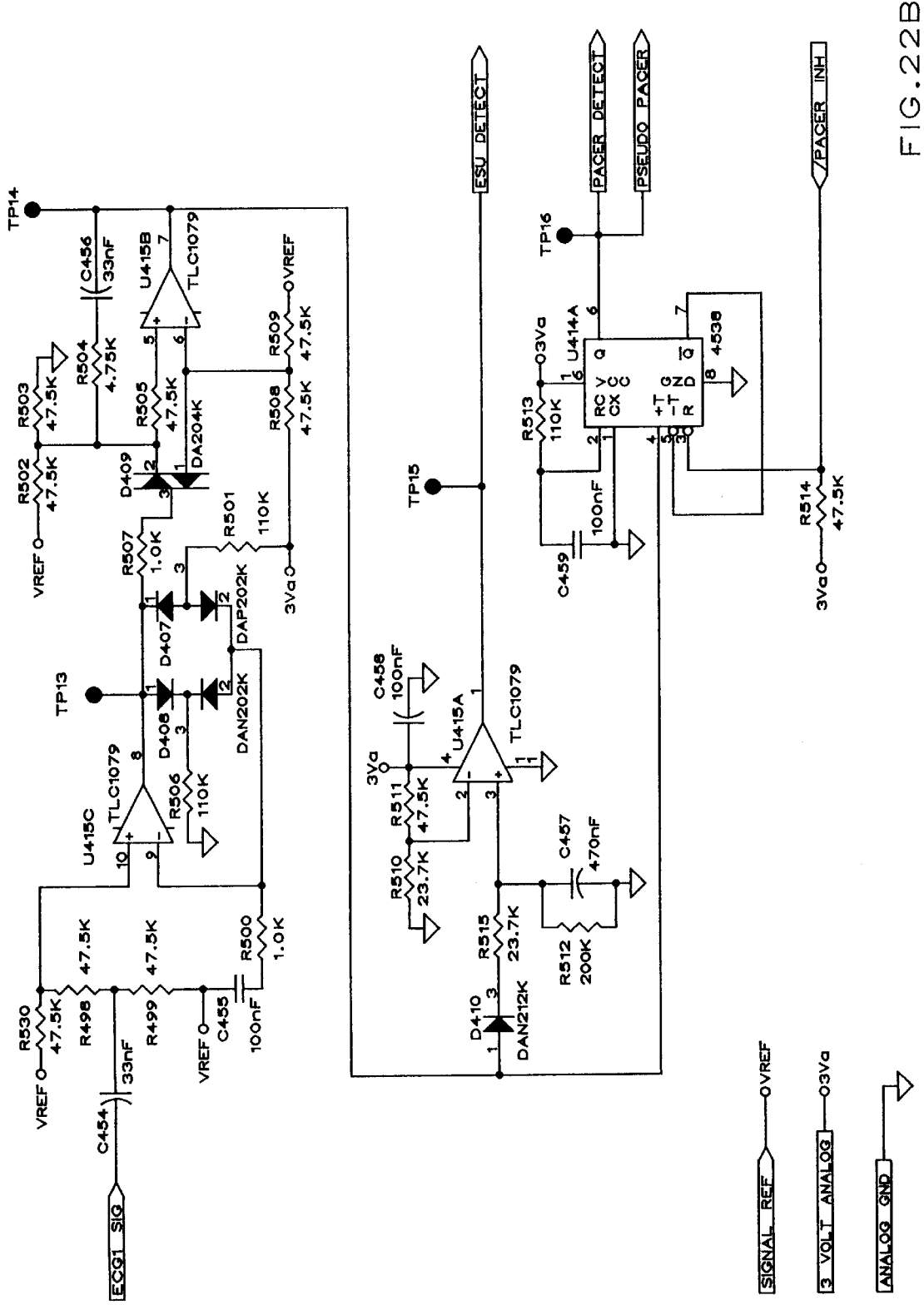
Figure 23:
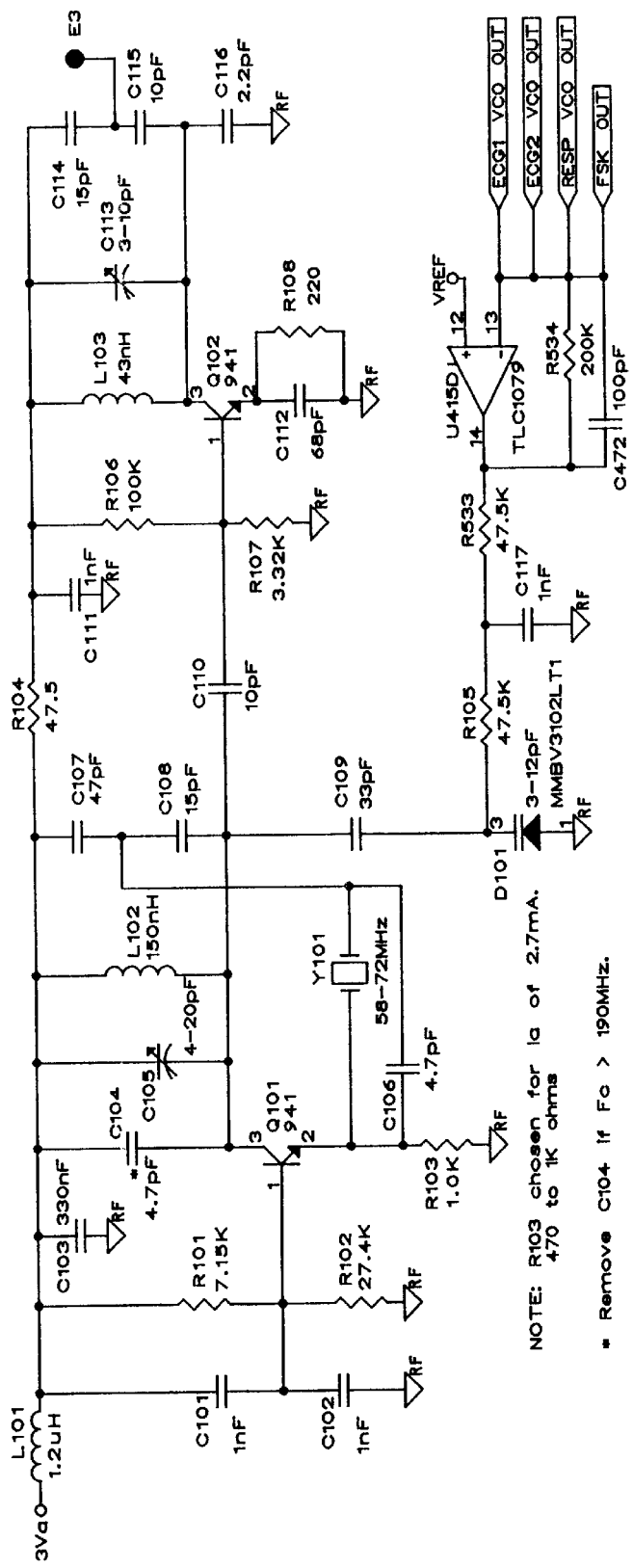
FIG. 23 is a schematic diagram of a second embodiment of the RF transmitter circuit of the remote patient monitoring device.
Figure 24:
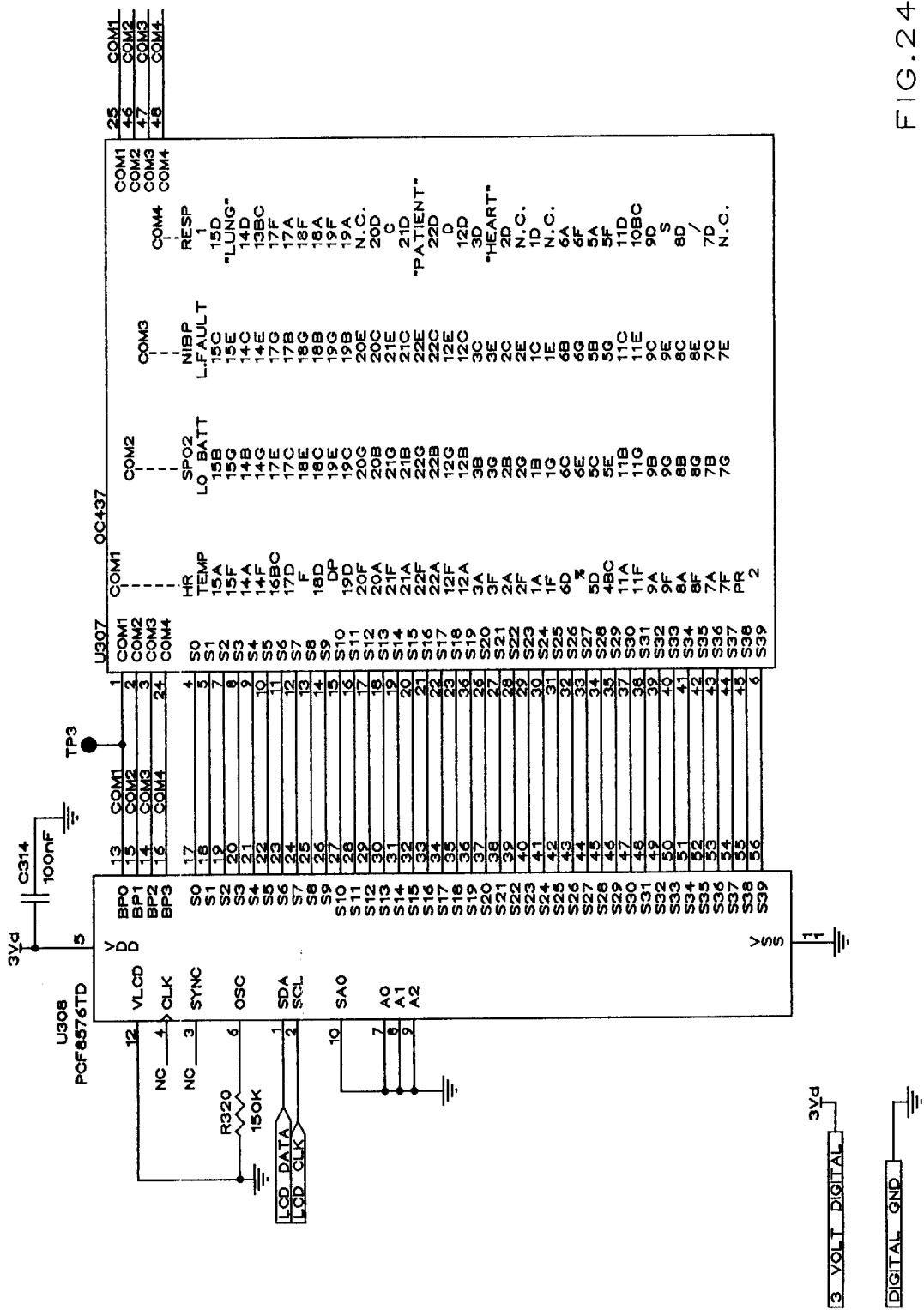
FIG. 24 is a schematic diagram of a second embodiment the LCD display circuit of the remote patient monitoring device.

FIG. 18 shows a second embodiment of the power supply circuit. As shown, the four standard AA batteries will provide 5 or more days of continuous operation, with the device 10 operating at a 50–55 mw power level.

Logic Control Circuit

Figure 2B:
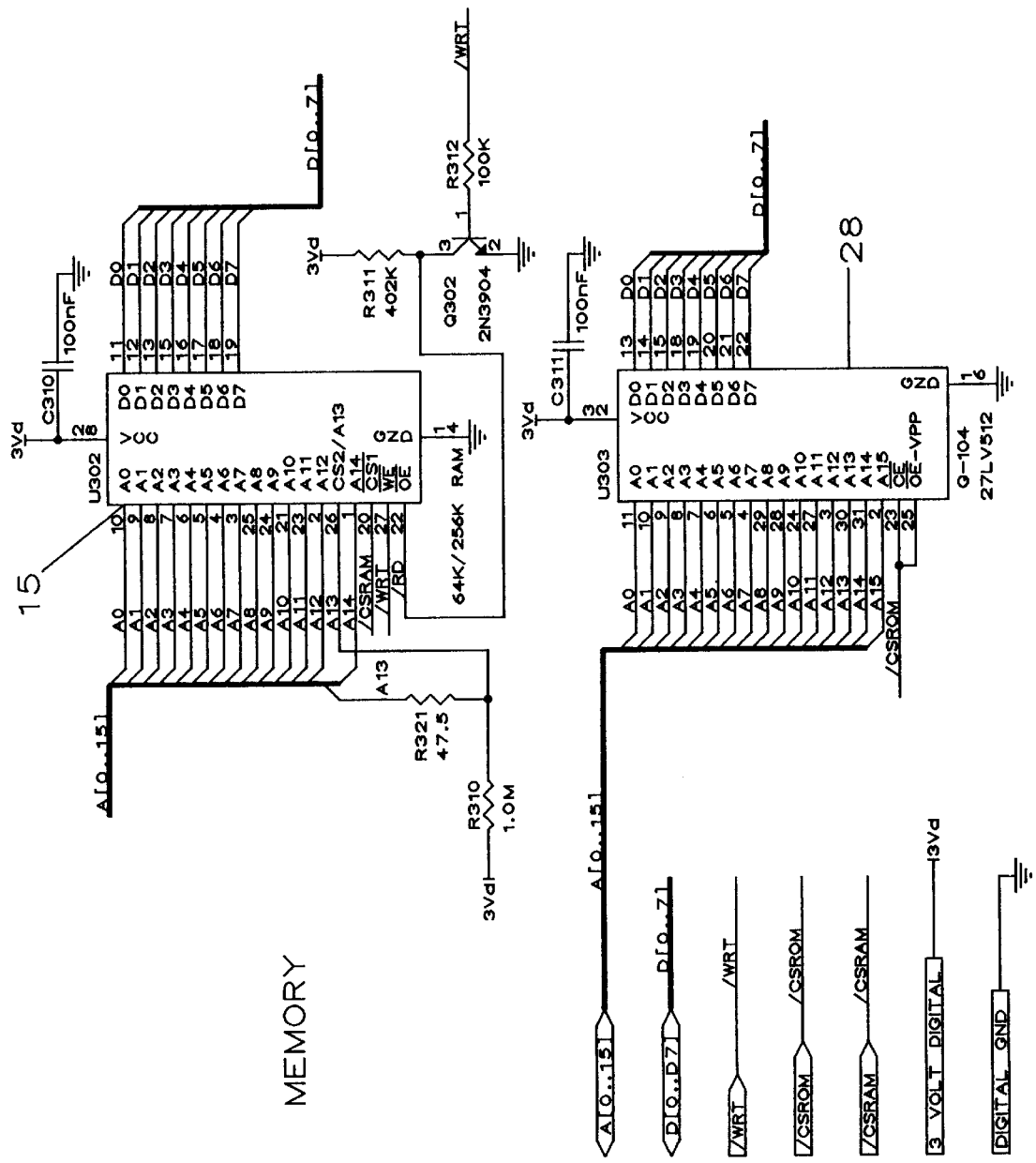
FIG. 2 is a schematic diagram of the main logic and power supply circuits of the remote monitoring device.
Figure 2D:
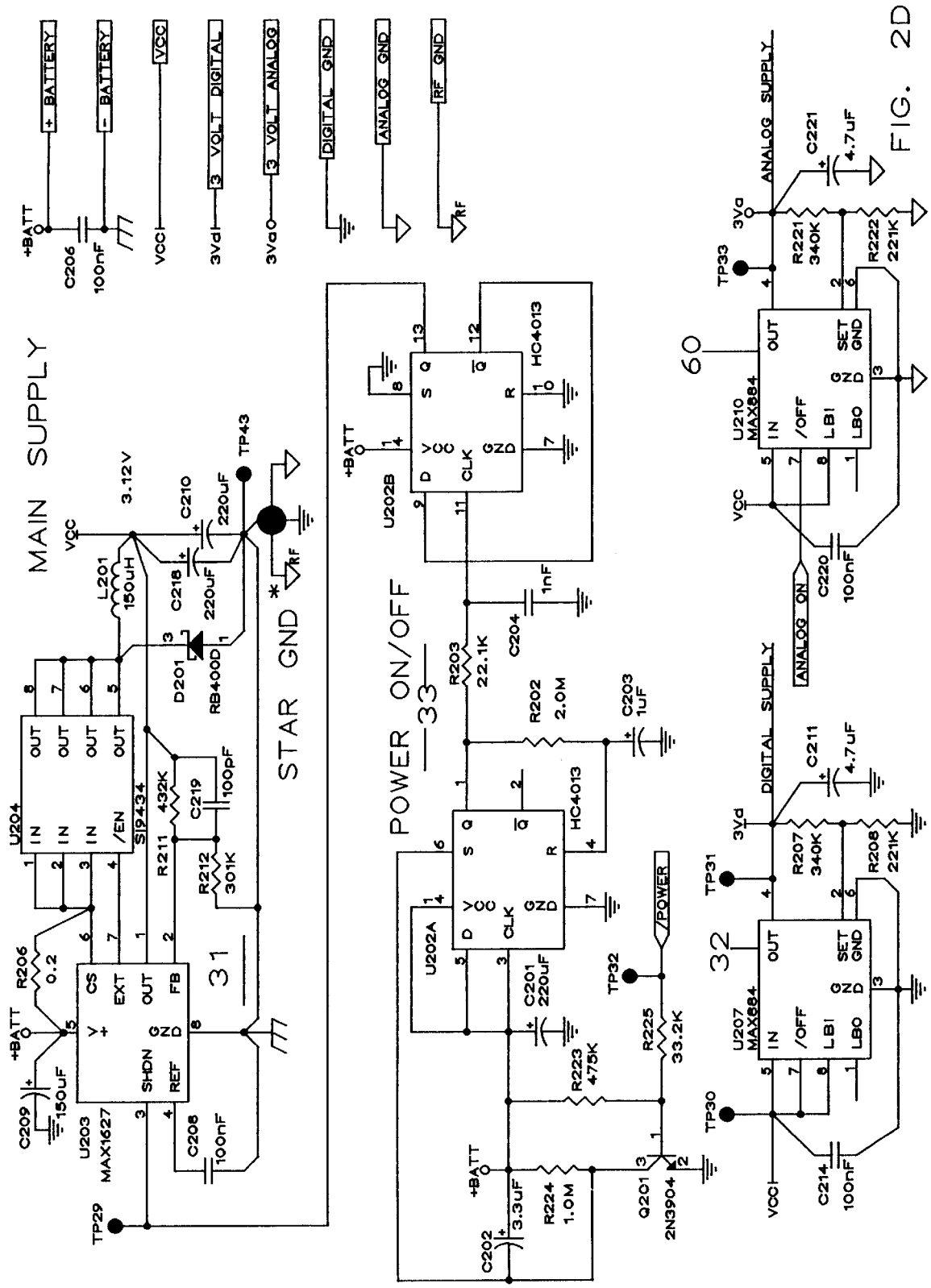
Figure 2E:
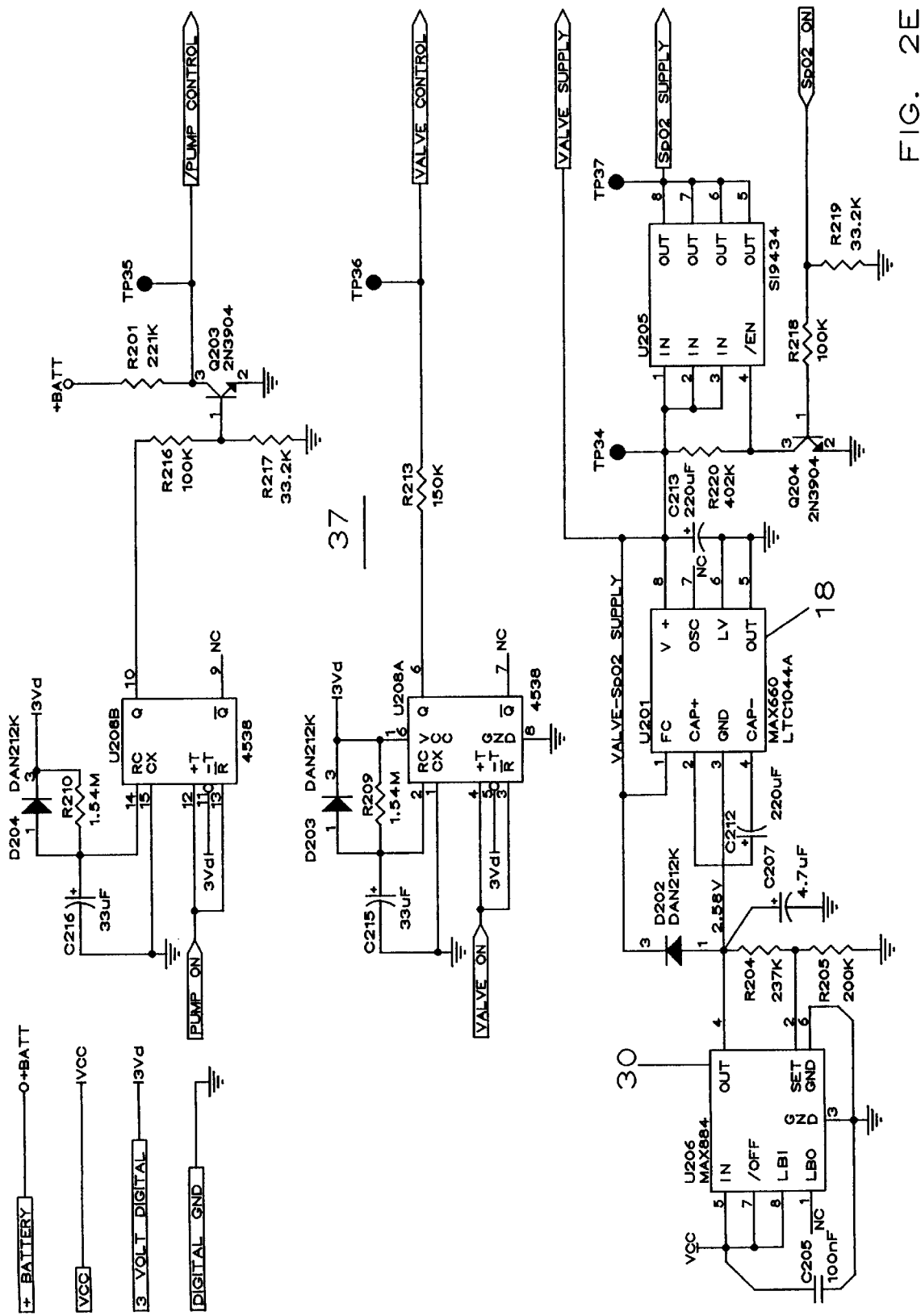

Referring to FIG. 2, overall logic control and processing of data by device 10 is determined by processor 14, preferably an industry standard 8 bit microprocessor, such as the Motorola MC68L11K1FU2. FIG. 2 shows the detail as to the interconnection of the processor 14 with the various other functional circuits and components in a preferred embodiment of device 10. In particular, the software which implements the various tasks of device 10 which will be discussed below and illustrated in FIGS. 11 through 16 is stored in software memory unit 28, preferably an OTPROM. Processor 14 is also capable of detecting a power failure in device 10, providing a POWER FAIL DETECT signal to power fail reset controller 29. Upon detection of the power failure, a RESET signal is generated by controller 29 to processor 14, which can then reset all functional units of device 10 to their initial state.

Processor 14 should also have integral analog to digital (A/D) conversion capabilities, with 8 bits of resolution and a sampling rate of 150 baud, to allow direct connection of vital sign data in analog format.

During processing of the raw vital sign data received from vital sign transducers 39, 53, 70, 77, 102, and 103, data being used and manipulated by processor 14 is dynamically stored in data memory unit 15, preferably an 8K random access memory chip.

As further illustrated on FIG. 2, the serial data input and output port of processor 14 is electrically connected to a serial port switch 36 which directs the RS232 port on processor 14 to either external debug/programming port 16 or to serial data received from pulse oximetry transducer 39.

Also shown on FIG. 2, and operatively connected to processor 14, is solid state driver module 37 which acts as a switchable high current source for the pump, dump valve, and bleed valve conventionally associated with blood pressure cuff transducers.

Processor 14 also has inputs to receive command signals from front panel switches 41a–d (FIG. 10). Switches 41a–d provide commands which, in accordance with the software stored in software memory 28, place device 10 into the calibrate mode, initiate manual non-invasive blood pressure measurement, place device 10 into an alarm standby mode, or cause transmission of a command which will initiate remote recording of patient vital signs at a central monitoring station. Processor 14 also has an input to receive a signal (ESU D. out) from noise detector and blocker circuit 62 (FIG. 7) so that when electrical interference is picked up from surgical equipment or other electrical equipment in the proximity, processor 14 will temporarily block the ECG wave form signals.

A modulated frequency shift keying (FSK) output is provided from processor 14, to digitally transmit parameter characters being displayed on display unit 42, at a preferred rate of 150 baud, with FSK modulation between 7000 and 7350 Hz.

Of course, processor 14 also has inputs to receive analog and digital pulse train ECG data from first and second channel ECG interface circuits 22 and 23, pulse oximetry data from pulse oximetry interface circuit 24, analog data from non-invasive blood pressure interface circuit 25, analog and digital pulse train data from respiration interface circuit 26, and analog data from temperature interface circuit 27.

The logic control circuit includes a ▓smart connector▓ function. If a transducer is not connected to the device 10, the corresponding vital sign measurement circuitry is turned off to prevent erroneous information from being displayed and transmitted. Thus, if a transducer is not hooked up when the device 10 is first activated, the corresponding vital sign parameter is never turned on. If the lead from the vital sign transducer is hooked up, the corresponding icon is displayed and vital sign data is transmitted. If the transducer connector subsequently comes loose, processing and transmission of the corresponding vital sign parameter is halted. If the transducer lead comes loose, a loose lead indicator is displayed.

ECG Interface Circuits

Figure 3A:
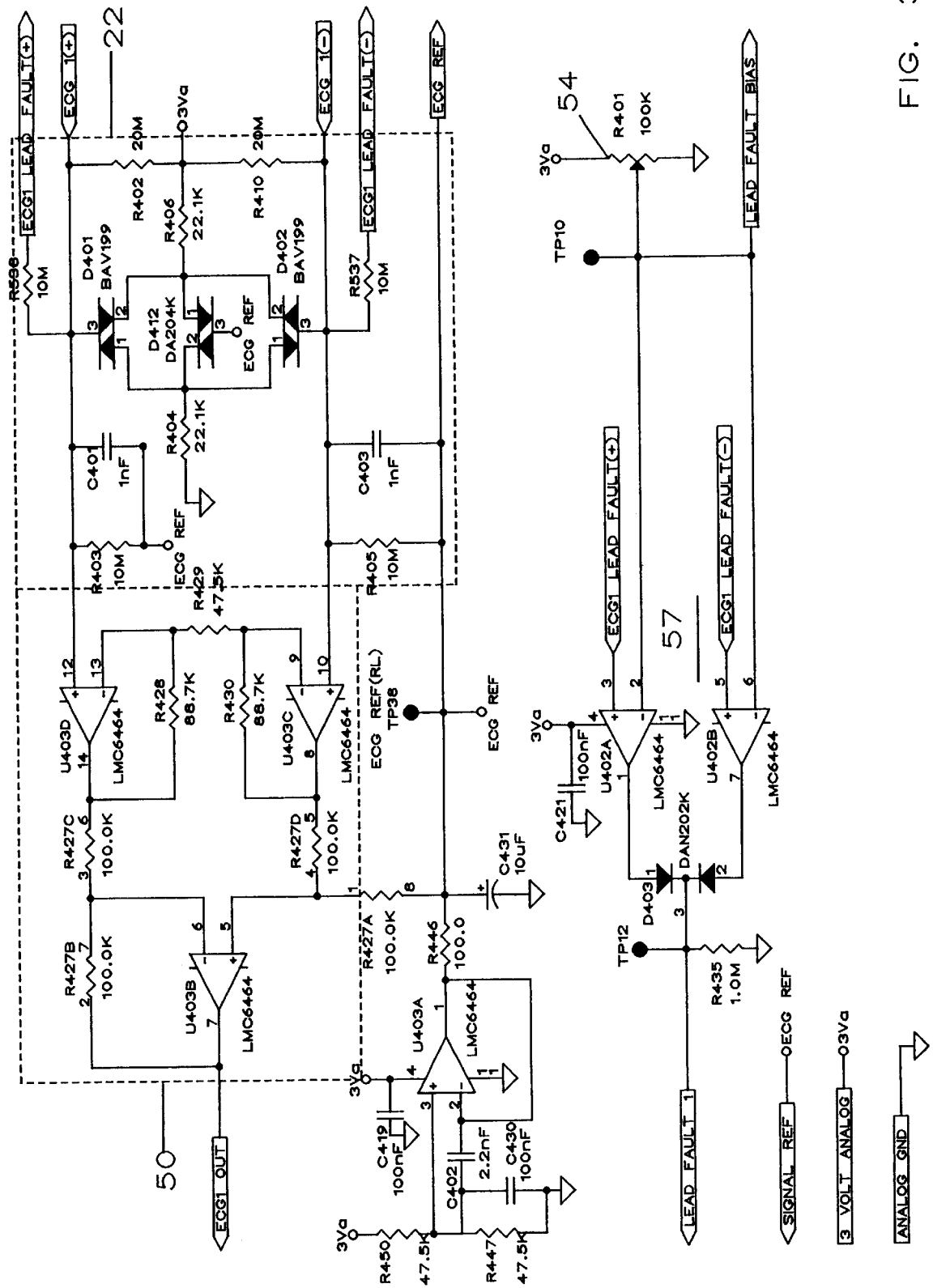
FIG. 3 is a schematic diagram of the first channel ECG interface and respiration interface circuits of the remote patient monitoring device.
Figure 3B:
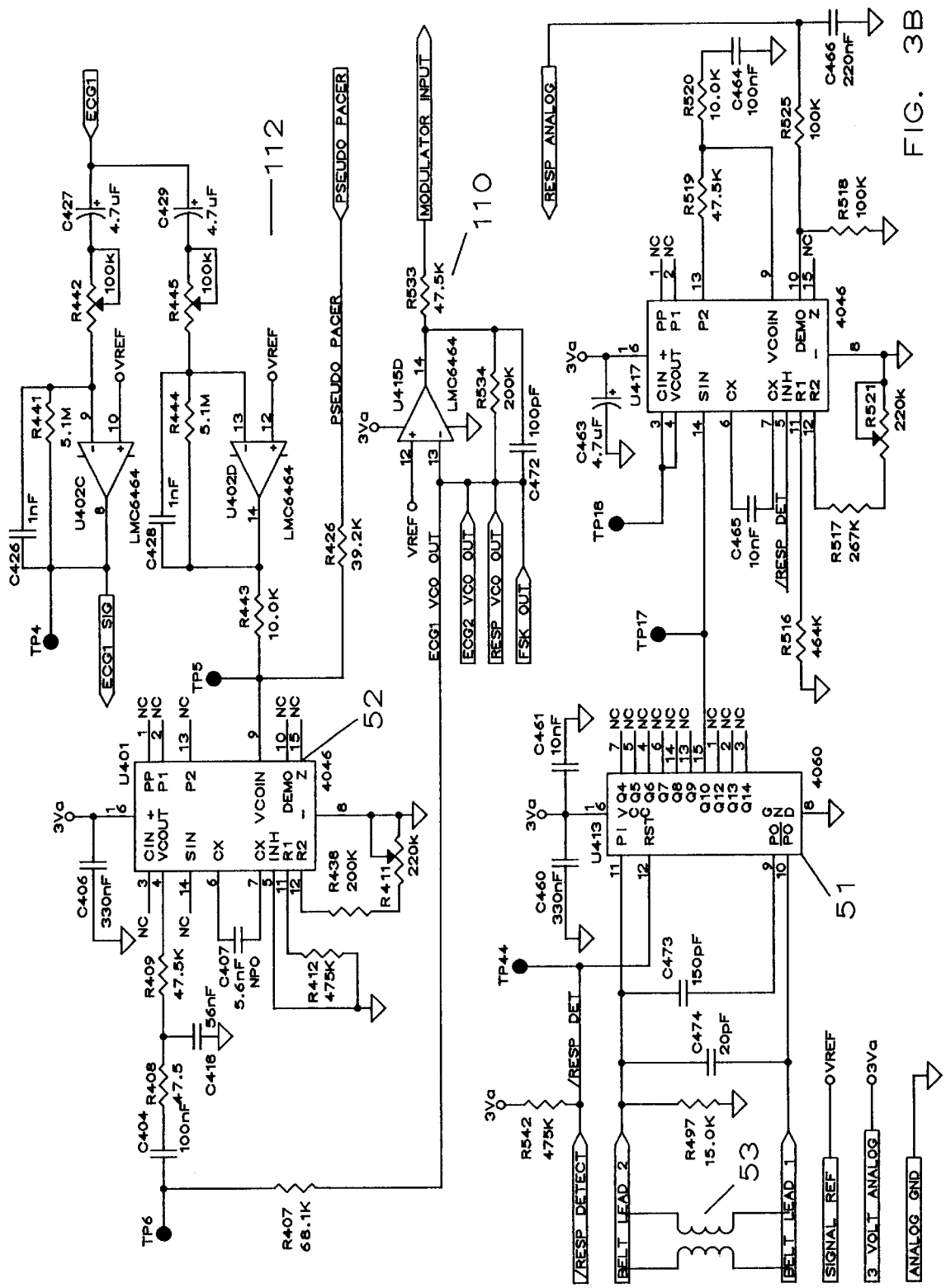
Figure 4A:
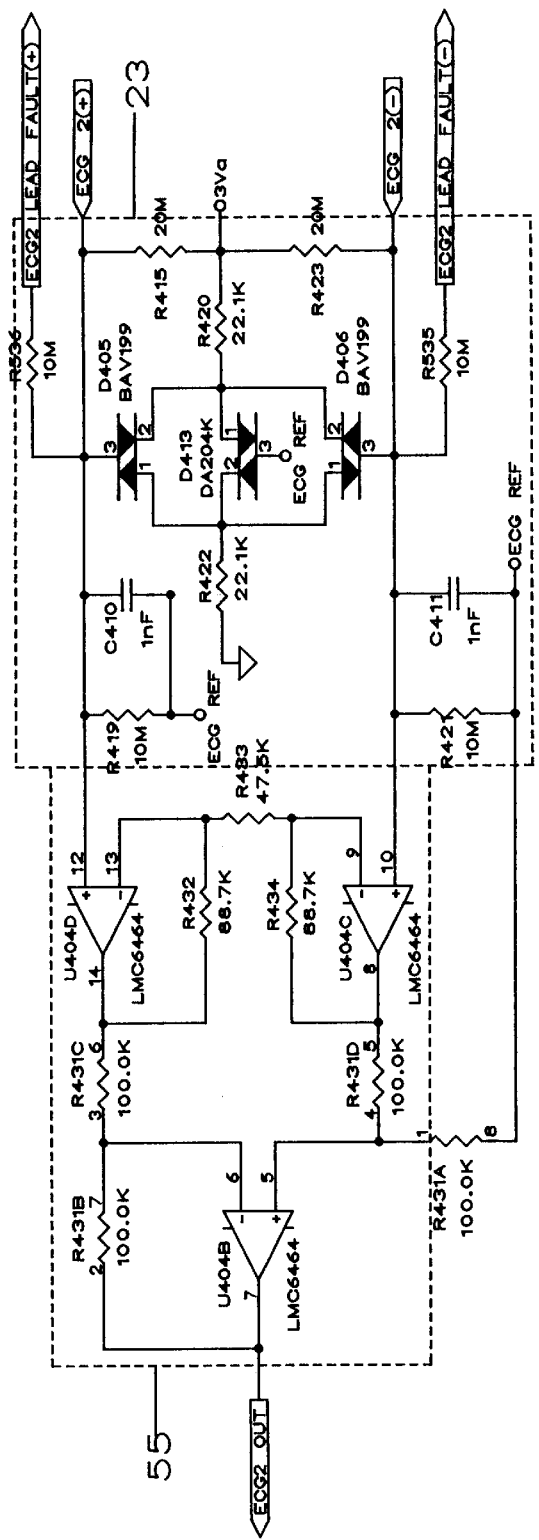
FIG. 4 is a schematic diagram of the second channel ECG interface circuit of the remote patient monitoring device.
Figure 4A:
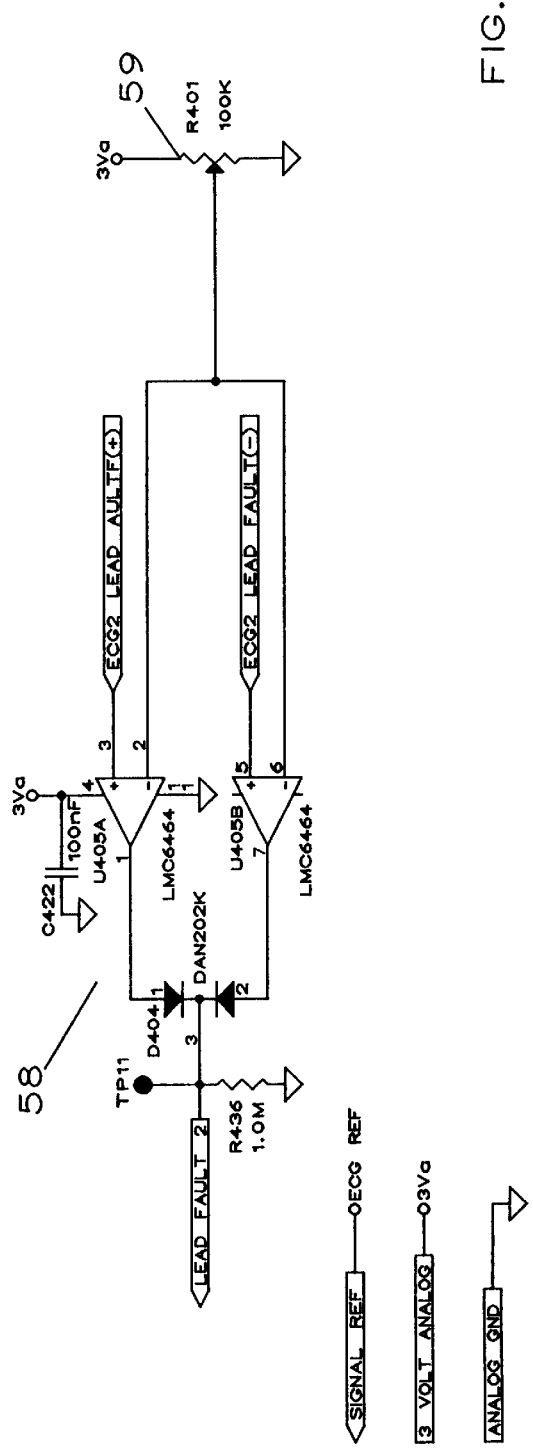
Figure 4B:
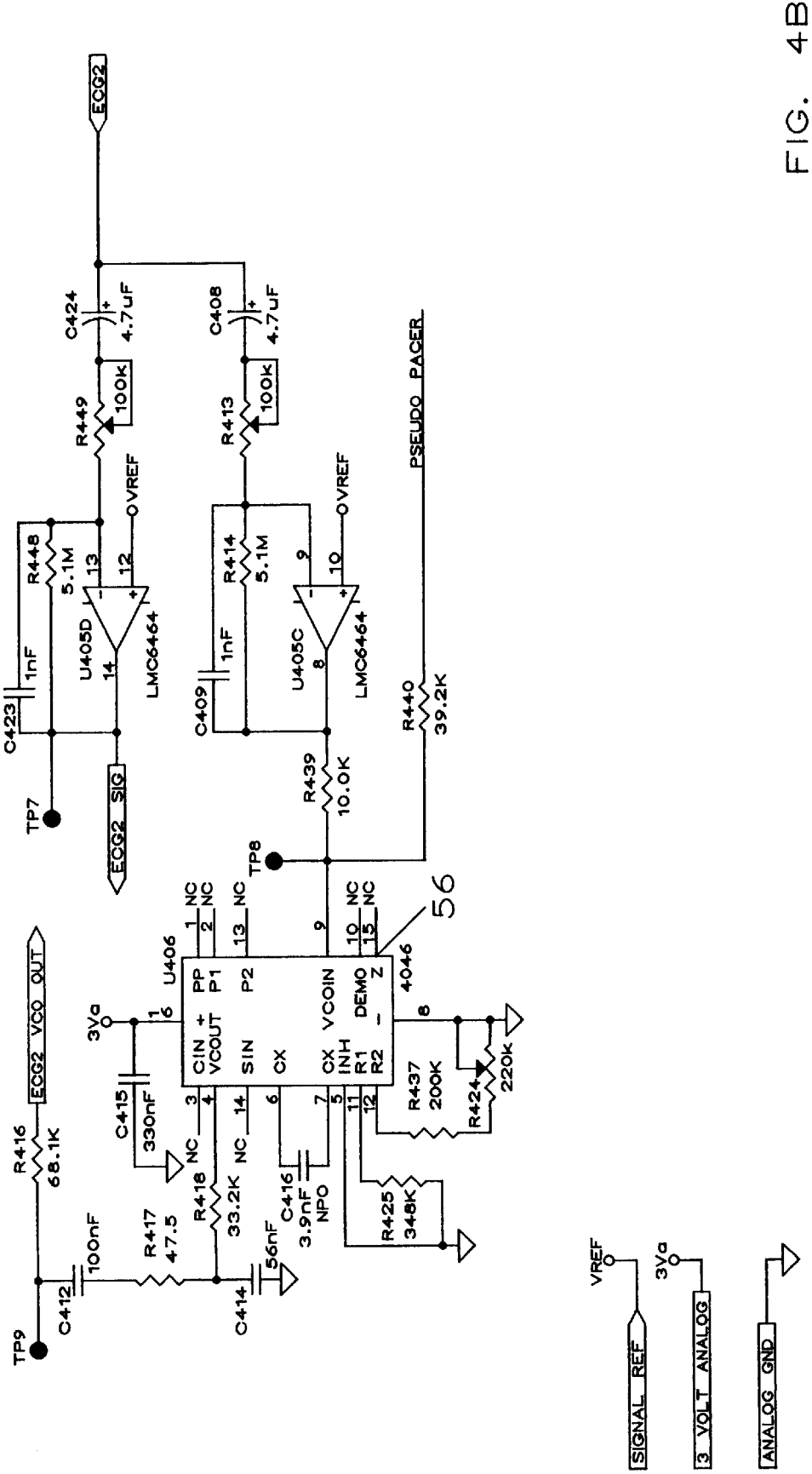

Preferably, two channels of analog ECG wave form monitoring are provided, as shown on FIGS. 3 and 4. Raw data received from first and second ECG transducers 102 and 103 (FIG. 1), which are attached to the patient in a conventional fashion (not shown) is received by first and second channel ECG interface circuits 22 and 23 which include signal conditioners 50 and 55. Signal conditioners 50 and 55 are preferably ASIC type integrated circuit devices, such as the Model PGS3 from PGS Medical, which are capable of conditioning the raw analog signals from the ECG transducers 102 and 103, by removing artifact and the like. Signal conditioners 50 and 55 also generate analog signals capable of reproducing conventional ECG wave forms on a display as well as a pulse train which can be supplied to processor 14 (FIG. 2) to determine the heart rate.

Figure 7A:
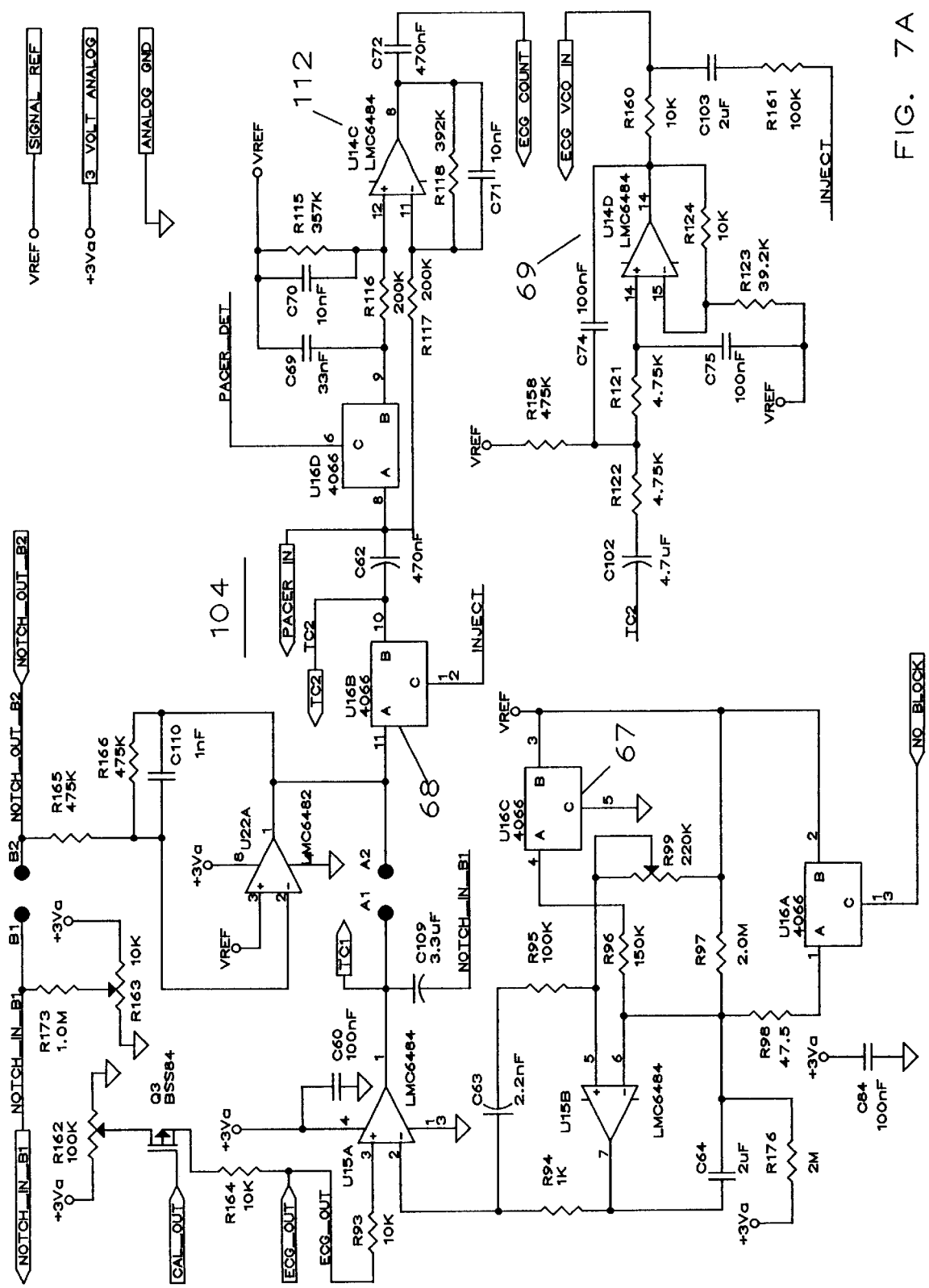
FIG. 7 is a schematic diagram of the pacemaker pulse and noise detector circuits of the remote patient monitoring device.
Figure 7B:
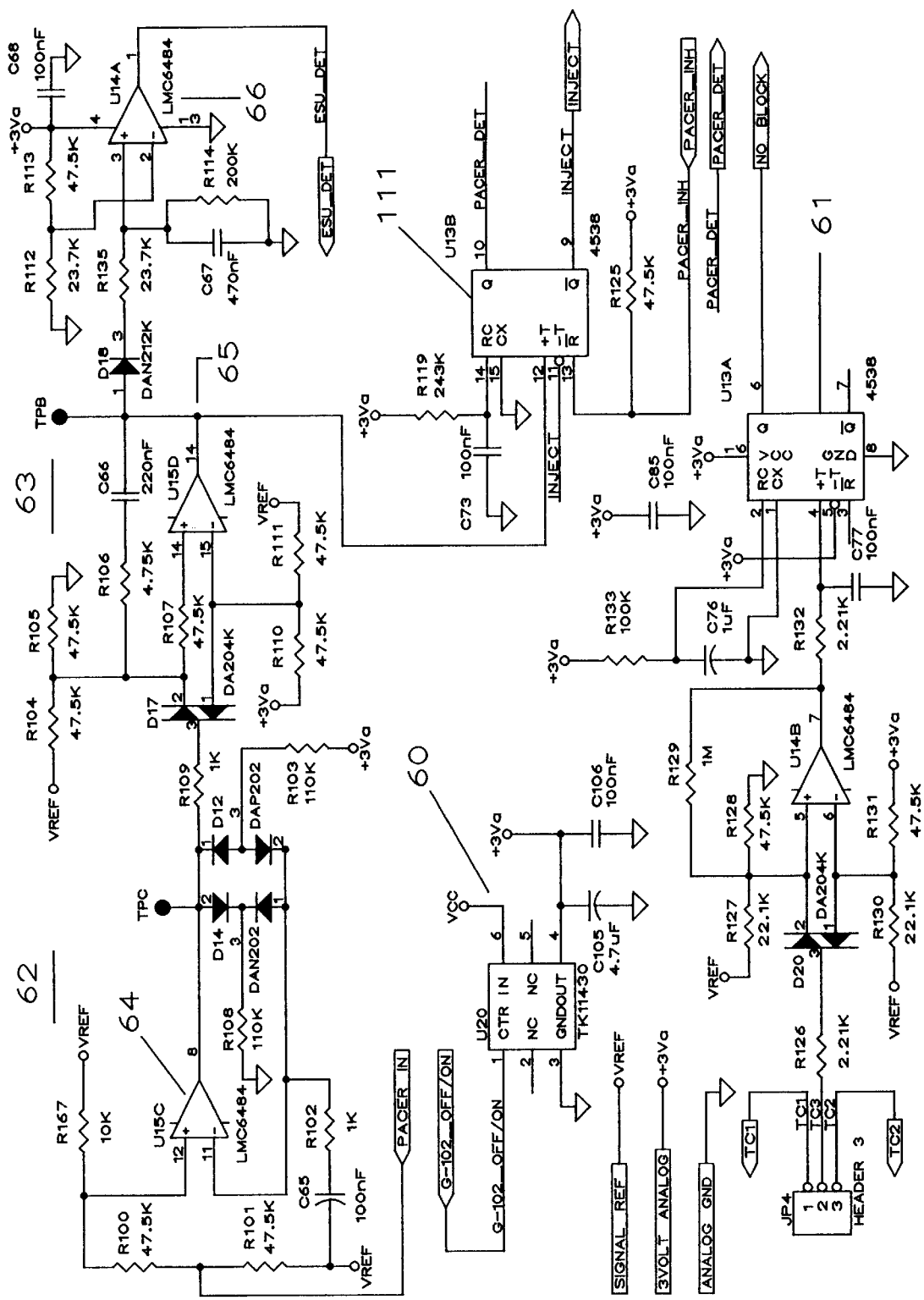

Looking at FIG. 3, the first channel ECG wave form data from signal conditioner 50, after further processing in the pacemaker and noise detection circuit 62 of FIG. 7, is supplied to voltage control oscillator (VCO) 52 as ECG1 VCO IN. VCO 52 converts the analog first channel ECG data to an FM signal which, after passing through operational amplifier 110, is supplied as modulated first channel ECG analog data to FM modulator circuit 91 of RF transmitter 21, shown on FIG. 8.

Also, the ECG interface circuits 22 and 23 are capable of detecting a failure or disconnection of one of the leads from ECG transducers 102 and 103, using loose lead alarm circuits 57 (FIG. 3) and 58 (FIG. 4). This causes first and second channel LOOSE LEAD signals to be supplied to processor 14 on FIG. 2. If a LOOSE LEAD signal is high for four seconds or more, processor 14 will display a "LOOSE LEAD" icon on display 42. If the lead fault is on Lead I the system will automatically change to Lead II preventing erroneous information in the patient chart.

Each ECG interface circuit 22 and 23 also includes threshold adjust means 54 and 59 for adjusting the heart rate detector threshold level.

Pacemaker Pulse and Noise Detector Circuits

FIG. 7 schematically illustrates noise detector and blocker circuit 62 as well as pacemaker pulse detector circuit 67 of device 10 which are electrically linked to both processor 14 and signal conditioner 50 of first channel ECG interface circuit 23. Noise detector and blocker circuit 62 includes a noise detector circuit 63, represented by series of operational amplifiers 64, 65, and 66 and their associated components. When interfering electrostatic units (ESU) are generated by adjacent electrical apparatus and detected, an ESU detector status signal (ESU D.out) is sent to processor 14 on FIG. 2. Processor 14 will then generate a pacemaker detector inhibit pulse (PAC INH) which is supplied to the input of switch 111 on FIG. 7, temporarily prohibiting ECG wave form output.

Also shown on FIG. 7 is pacemaker pulse detector circuit 67, the function of which is to detect on the first channel raw ECG data, the presence of an electrical pulse generated by a pacemaker being used for the benefit of the patient. A typical pulse generated by a pacemaker (pacer pulse) is too narrow to be handled by device 10. Therefore, upon detection of a pacemaker pulse by pacemaker pulse detector circuit 67, a PACER DET signal is sent to processor 14. In response, a wider (10 ms, 300 mvolt) pseudo pacemaker pulse is generated by pulse injector switch 111. The injection of a pseudo pacemaker pulse also causes ECG signal switch 68 to temporarily shut off the processed analog ECG signal. A high speed integrator 61 is also includes in noise detector and blocker circuit 62, for purposes of removing DC voltage shifts in the ECG wave form base line.

Pulse amplifier circuit 112 extracts from the raw first channel ECG wave form data information to generate a first channel ECG COUNT signal which, when returned to the appropriate signal conditioner 50 or 55 and converted to a logic compatible signal (ECG1 or ECG2 PULSE OUT), is sent to the processor 14 for heart rate determination.

Pacemaker pulse detector circuit 67 includes op amps 64 and 65.

A notch filter 104 is also part of noise detector and blocker circuit 62. Its function is to remove 60 Hz line noise passed into device 10 from the various external connections to the vital sign transducers.

DC restore circuit 111 restores and maintains the DC level of the ECG waveform data during processing by noise detector and blocker circuit 62 as well as pacemaker pulse detector circuit 67.

Respiration Interface Circuit

Preferably, device 10 will have a respiration interface circuit 26 to an inductance pneumography respiration belt transducer 53, shown on FIG. 3. Respiration transducer 53 provides a signal having a frequency which varies in response to movement of respiration transducer 53 as the patient breathes, nominally in the range of nine hundred sixty kilohertz (960 Khz). Ripple counter 51 divides the signal from respiration belt 53 such that the output is in the range of 960 Hz. The resulting RESP SENSE signal is supplied to the signal input of voltage control oscillator 81, which is part of the respiration detector circuit 80 of FIG. 6.

Respiration detector circuit 80 includes a respiration count stage 83 which processes the modulated respiration data from VCO 81 to generate a respiration count (RESP COUNT) signal for processor 14.

In addition, if respiration alarm circuit 82 senses that VCO 81 is not locked, being outside its nominal locked range of seven hundred fifty-four (754) to one thousand three hundred fifty (1350) HZ, an alarm (SENSOR ALARM) signal is communicated to processor 14 to indicate that there is no respiration belt transducer 53 connected to device 10.

RF Transmitter Circuit

Figure 8:
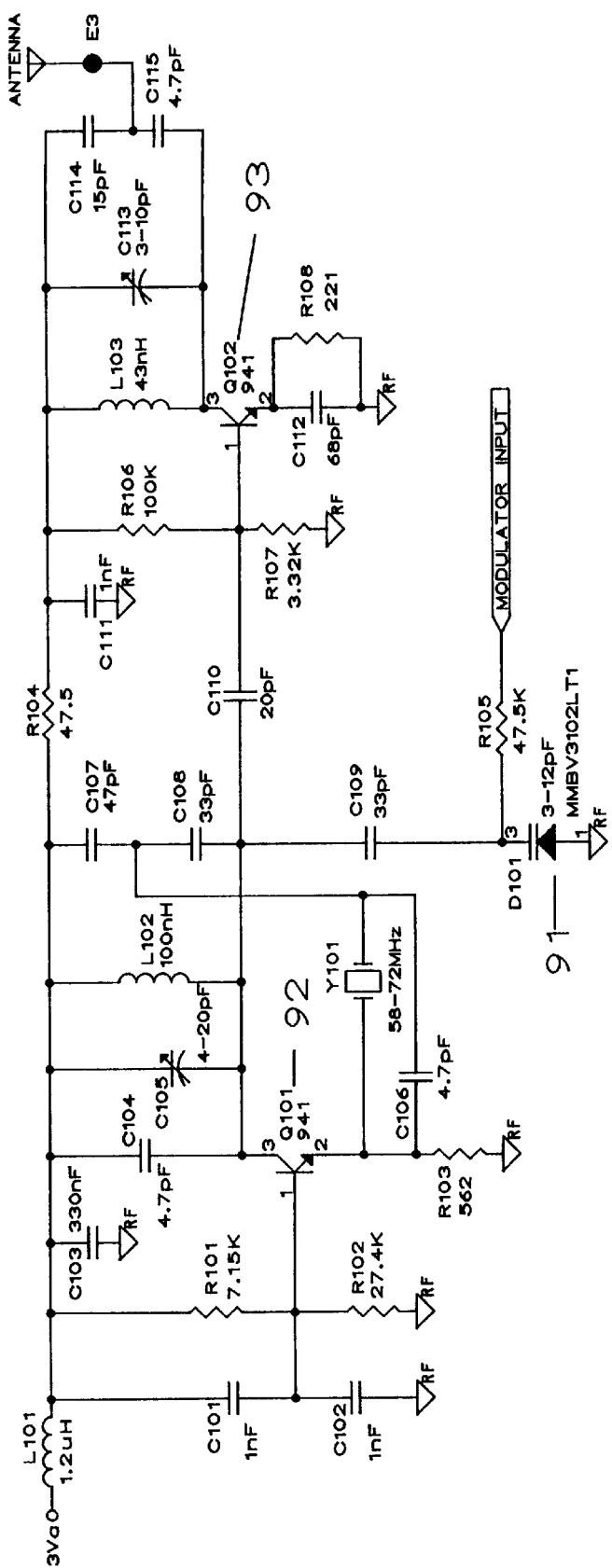
FIG. 8 is a schematic diagram of the RF transmitter circuit of the remote patient monitoring device.

FIG. 8 is a schematic diagram of the RF transmitter circuit 21 of device 10. In a preferred embodiment, RF transmitter circuit 21 includes two stages, the first stage being a third overtone oscillator circuit 92 which will generate a signal in the VHF range, and an FM modulator circuit 91. In the embodiment of FIG. 8, FM modulator circuit 91 uses a varactor diode to vary the operating frequency of oscillator circuit 92, providing FM modulation for the final amplifier stage 93 of RF transmitter circuit 21. The signal input (MODULATION INPUT) for modulator circuit 91 is received from modulation summer/amplifier 110 (FIG. 3), and will include the first and second channel ECG wave form outputs (ECG1 and ECG2 VCO OUT) from voltage control oscillators 52 (FIG. 3) and 56 (FIG. 4), as an analog ECG wave form superimposed over the FSK digital data transmitted by the FSK output signal (FSK LINK) from processor 14 (FIG. 2). Analog respiration waveform data from respiration interface circuit 26 is also superimposed over the FSK data. In this way, RF transmitter 21 can simultaneously transmit digitized vital sign information, as displayed on device 10 LCD display 42, along with first and second channel ECG and respiration wave form information.

Blood Pressure Interface Circuit

Figure 5A:
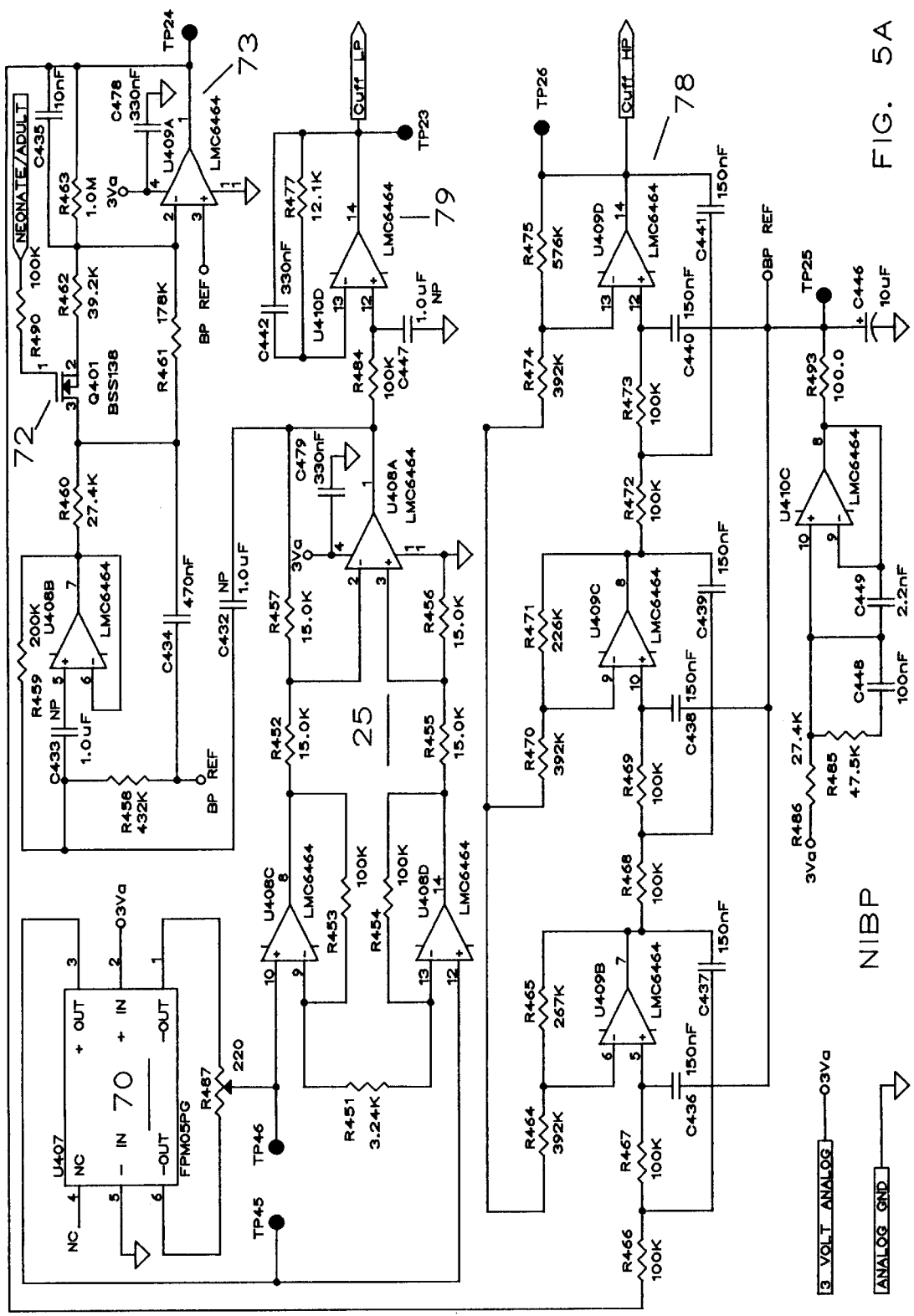
FIG. 5 is a schematic diagram of the blood pressure and temperature interface circuits of the remote patient monitoring device.
Figure 5B:
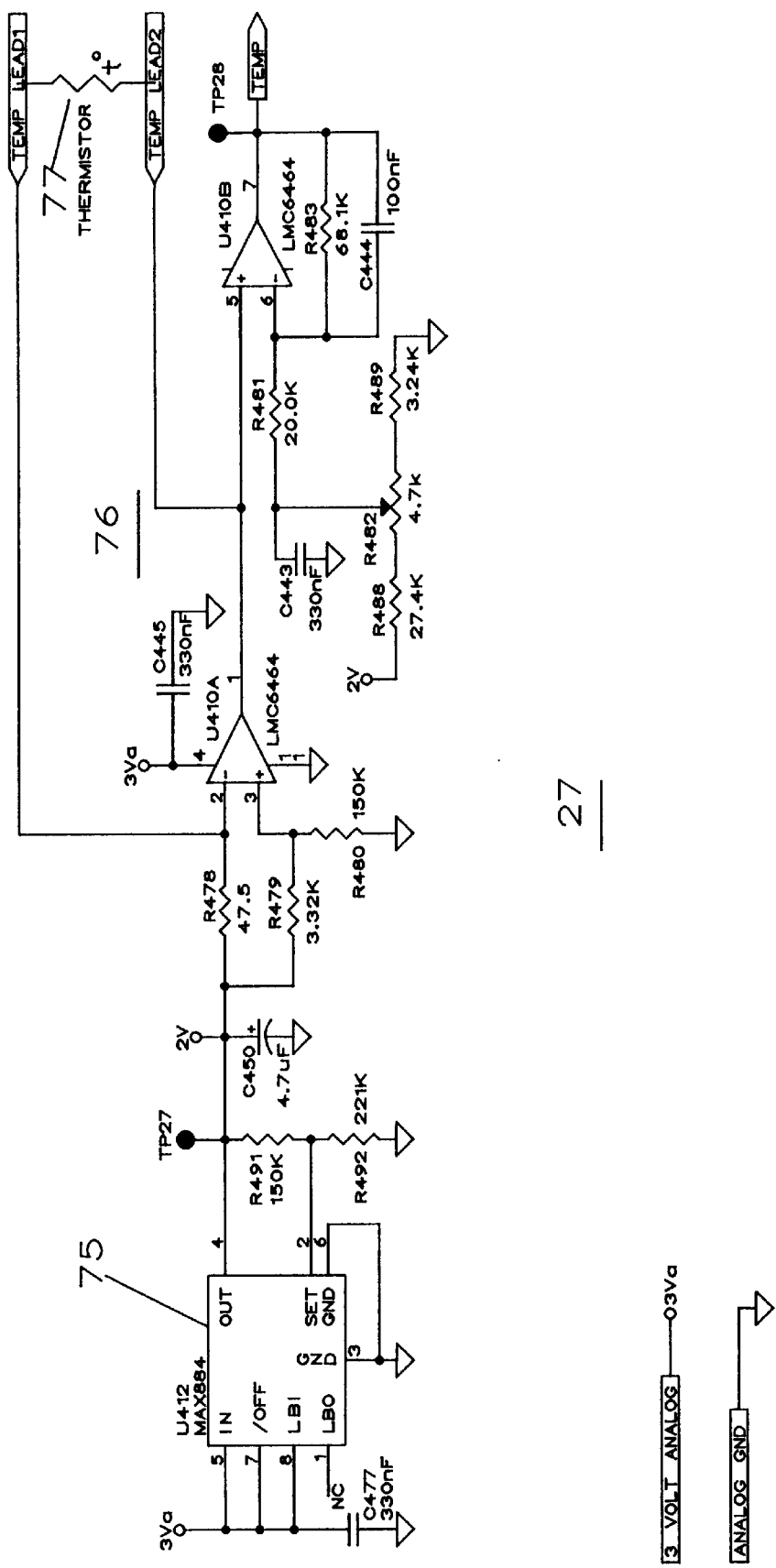

Details of blood pressure interface circuit 25 are shown on the upper portion of FIG. 5. A controllable blood pressure cuff transducer 70 is attached to the patient such that cuff transducer 70 can be activated manually by the front panel switch 41d (FIG. 10) or at regular intervals programmed within device 10. The blood pressure interface circuit 25 has its own voltage regulator 71 which is operated by a blood pressure power control signal (BP PWR CNTRL) generated by processor 14. The systolic and diastolic blood pressure data received from transducer 70 is amplified and conditioned in interface circuit 25, resulting in a blood pressure cuff high point signal (CUFF HP) 78 and a low point signal (CUFF LP) 79, which are used by processor 14 to generate a digitized diastolic and systolic blood pressure reading for LCD display 42.

To account for the difference in blood pressure signal levels obtainable from an adult patient as compared to an infant patient, the user of device 10 can cause processor 14 to switch (NEONATE/ADULT) blood pressure interface circuit 25 between adult and infant modes using switch 72, the effect of which is to vary the gain of amplifier stage 73 and lower the maximum operating pressure to 140 mm Hg.

Temperature Interface Circuit

The temperature interface circuit 27 is further illustrated on the lower portion of FIG. 5. Temperature probe transducer 77 presents a resistance to the input of interface circuit 27. The resistance varies in response to a change in temperature measured on the patient. This variable resistance is sensed by temperature detector circuit 76, along with a reference voltage generated by reference voltage unit 75. Ultimately, interface circuit 27 generates an analog temperature signal (TEMP) which is provided to an input of processor 14 (FIG. 2). Processor 14 then converts the signal to a digital display of the patient's temperature, either in degrees Centigrade or Fahrenheit, as selected by the user of device 10.

Operation of the Remote Patient Monitoring Device

Control of the various tasks and routines of device 10 is handled entirely by software associated with processor 14 and program memory unit 28 (FIG. 2), subject to override or interruption by operation of front panel switches 41a–d (FIG. 10). Each function, routine, or task is separately described in FIGS. 11 through 16. Accordingly, to operate device 10, the user first connects ECG transducers 102 and 103, pulse oximetry cuff transducer 39, blood pressure cuff transducer 70, respiration belt transducer 53, and temperature probe transducer 77 to their respective hardwired inputs on device 10.

Figure 11:
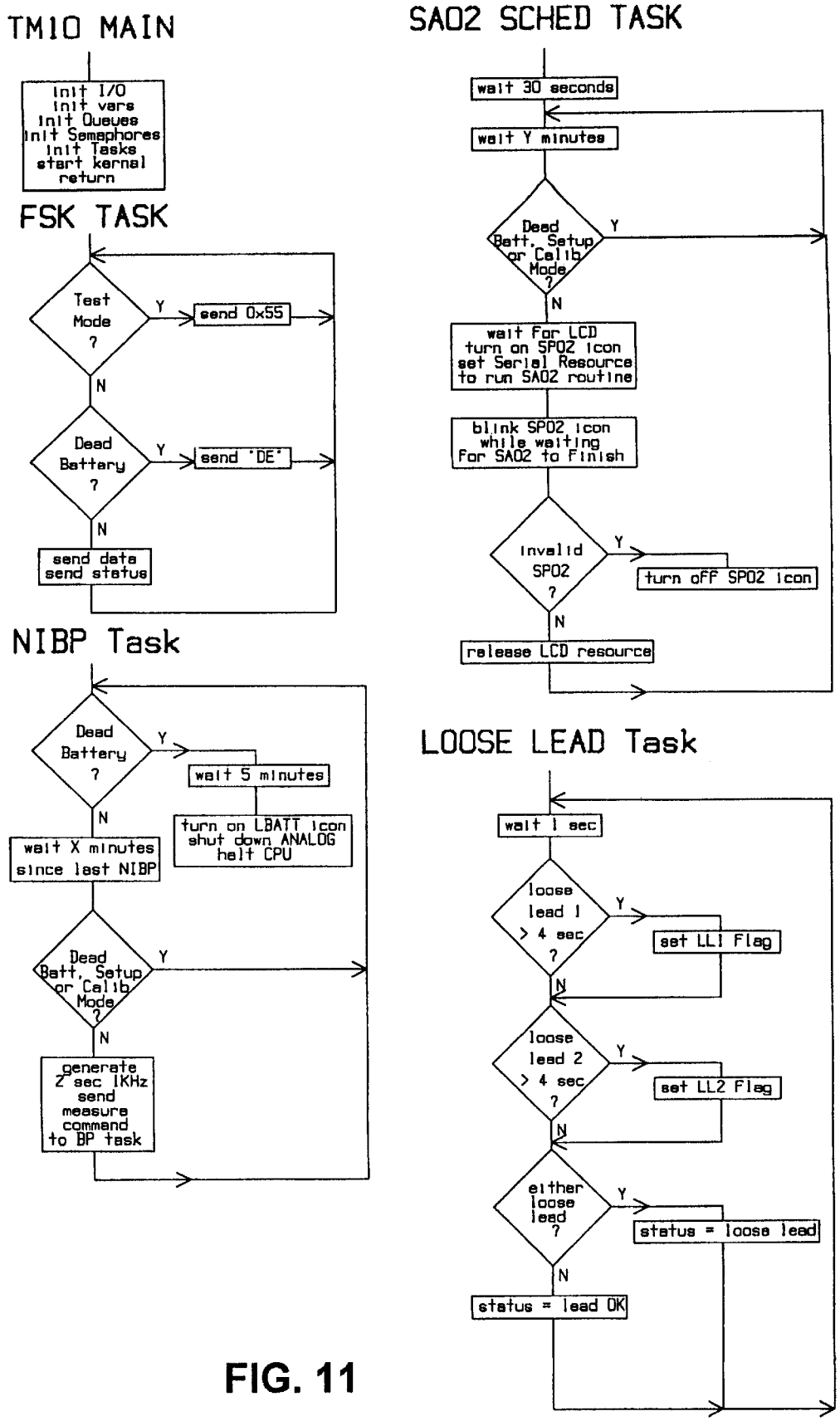
FIG. 11 is a flow chart showing the sequence of operations that occur within the remote patient monitoring device during device start-up, and during the FSK, NIBP, SpO2 SCHEDULE, and LOOSE LEAD Tasks.

Referring first to FIG. 11, device 10 is turned on by pressing and holding alarm/standby switch 41a, placing processor 14 into the main initialization task. This causes initialization of all input and output ports, all processor data variables, data queues, and semaphores, and turns over control of all tasks to the core program, or kernel. All parameter high and low alarm limits are set at the factory determined presets. Should a parameter exceed these limits an audible and visual indicator is presented at the device and the remote location. An alarm signal is sent to the remote location even if the alarms are turned off at the device 10. Each of the high and low alarm limits for each of the six parameters is user settable. The kernel preferably runs the highest priority (lowest numbered) task that is ready to run and that is not blocked by some other condition. Typically, the highest priority tasks are those needing the fastest response, such as blood pressure measurement tasks which must perform signal processing in real time. The lowest priority tasks are those where response time is not as critical, for example, the task for driving LCD display 42, the DEBUG task, and the flashing display LED heart beat display task.

The kernel portion of the program also manages the semaphores and queues. The semaphores are used as "yes-no" flags between tasks, and the queues are first-in first-out buffers for intertask communications.

Preferably, the lowest level hardware interactions are handled by interrupts in a conventional manner. The interrupt handlers respond to an interrupt signal from a peripheral unit, such as a transducer interface circuit, and quickly services that unit, buffering the transaction so that one of the tasks can deal with the buffered data when the task has an opportunity to run.

In the preferred embodiment of device 10 as described, there are seven semaphores. The Serial semaphore is used as a resource lock so that the DEBUG and pulse oximetry ($SpO_2$) tasks can share the same serial port. The $SpO_2$ semaphore is set by the SpO2 scheduler task to tell the $SpO_2$ task to run. A blood pressure (BP) semaphore is set by the BP Scheduler Task and tells the BP Scheduler Task to run and take a blood pressure measurement. The BP Done semaphore is also set by the BP Task and tells the BP scheduler that the BP Task is finished so that the BP scheduler can relinquish the resources it needed. The Display semaphore is a "round robin" semaphore for sharing the resources of the display and driver 42 and 43. The ESU Detect semaphore is set when the ESU input goes high, allowing the Pacer Inhibit Task to drive the pacer inhibit signal (PACER INH) low for four seconds. The Cal Push Button semaphore is set when front panel system switch 41c is pressed.

In addition, there is one data queue. The plethysmography data (which is not reported in this embodiment) to the Pleth output is queued during pulse oximetry measurements.

There are four interrupt handlers. A "serial port character received" interrupt causes serial port received characters to be stored in a FIFO buffer which is in turn polled by tasks needing input from the serial port. An output compare 4 interrupt is fired by a timer every one bit time for the one hundred fifty (150) baud FSK data transmission so that the FSK frequency can be driven entirely in software. This interrupt simulates the use of a UART port on processor 14 which is occupied by other functions and is not available for use. Therefore, the output compare 4 interrupt functions as an internal timer in software to set the FSK baud rate.

Input capture 1–4 interrupts are used to measure the period of the ECG1, ECG2, RESP, and pacemaker (PACER) inputs. Thus, the input capture 1–4 interrupts establish the sample rate for the ECG1, ECG2, RESP, and pacemaker measurements based on the clock speed of processor 14. The Timer Overflow interrupt is used to turn the sixteen (16) bit hardware timer into a thirty-two (32) bit timer by counting the overflows in a sixteen (16) byte integer.

Finally, the Real Time interrupt is programmed to interrupt every four milliseconds, which the kernel uses as its clock for measuring time delays and doing task switching. The analog to digital converter in processor 14 also samples on this interrupt to provide a steady supply of two hundred fifty (250) hertz samples for the Blood Pressure Task.

FSK Task

The FSK Task is shown on FIG. 11. This task runs continuously, transmitting display data generated by processor 14 as an FSK output data stream to RF transmitter circuit 21. Preferably, the FSK output is modulated between 7000 Hz and 7350 Hz. Priority of this task is 32.

Loose Lead Task

Also shown on FIG. 11, a Loose Lead Task checks for a loose ECG transducer lead signal (LOOSE LEAD 1 on FIG. 3 and LOOSE LEAD 2 on FIG. 4) every second, providing a lead fault bit in the device status word of processor 14 where appropriate. Priority is 20.

Pulse Oximetry ($SpO_2$) Schedule Task

Shown on FIG. 11, the $SPO_2$ Schedule Task is run at regular intervals, as programmed by the user of device 10 and stored in program memory 28.. Assuming that device 10 is not in a dead battery, set up, or calibration mode, the SPO2 Schedule Task waits for the availability of display 42, turns on the pulse oximetry icon, and then sets the serial resources of processor 14 to run the Pulse Oximetry ($SPO_2$) Task, blinking the pulse oximetry icon while waiting for the task to finish.

Blood Pressure Task

The Blood Pressure (NIBP) Task also checks for a dead battery and waits for the BP Semaphore. Again, if a dead battery status is maintained for five minutes, it turns on the low battery icon on display 42, shuts down analog signal processing, and halts processor 14. Otherwise, the NIBP Task functions periodically on intervals set by the user of device 10 and then generates appropriate command signals to cause the measurement of non-invasive blood pressure. During the Blood Pressure Task, if device 10 does not sense a rise in pressure in transducer 70 to twenty mm HG after ten seconds, it will assume that the cuff transducer 70 is not plugged in, report NIBP is missing and systolic and diastolic pressure is at zero. In the time that device 10 is performing the NIBP measurement, it does not service the "lung" icon on display 42, thereby freezing it. The "heart" icon on display 42 will blink during the bleed down phase as device 10 detects pulses from cuff transducer 70. After this task is run, it sets the BP Done Semaphore. Priority is 26.

Display Task

Figure 12:
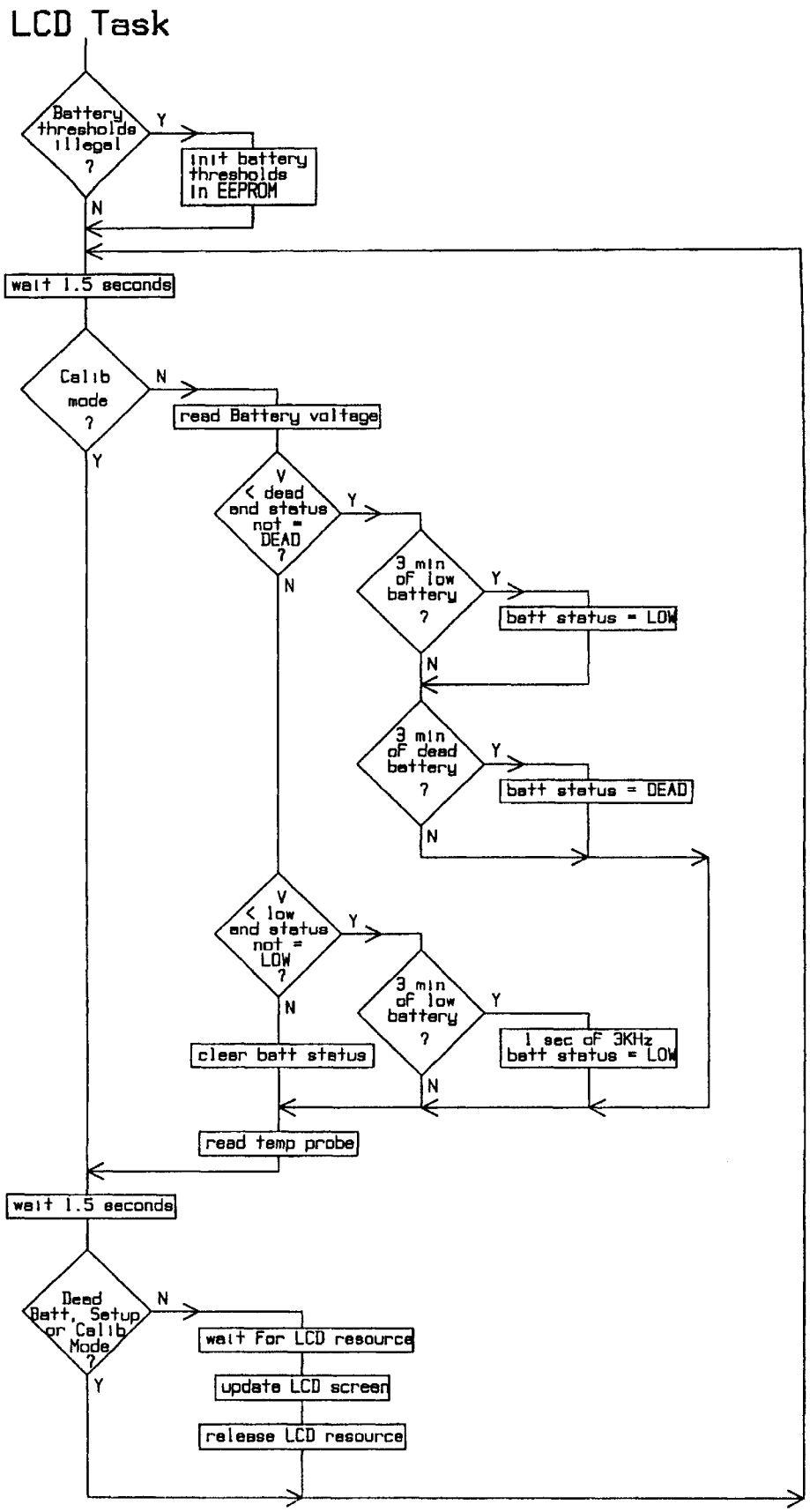
FIG. 12 is a flow chart showing the sequence of operations that occur within the remote patient monitoring device during the LCD T Task.

The LCD T Task is shown on FIG. 12. This task includes measurement of battery voltage to determine battery status, along with continuous updating of display 42 as data is generated. Priority is 22.

Debug Task

Figure 13A:
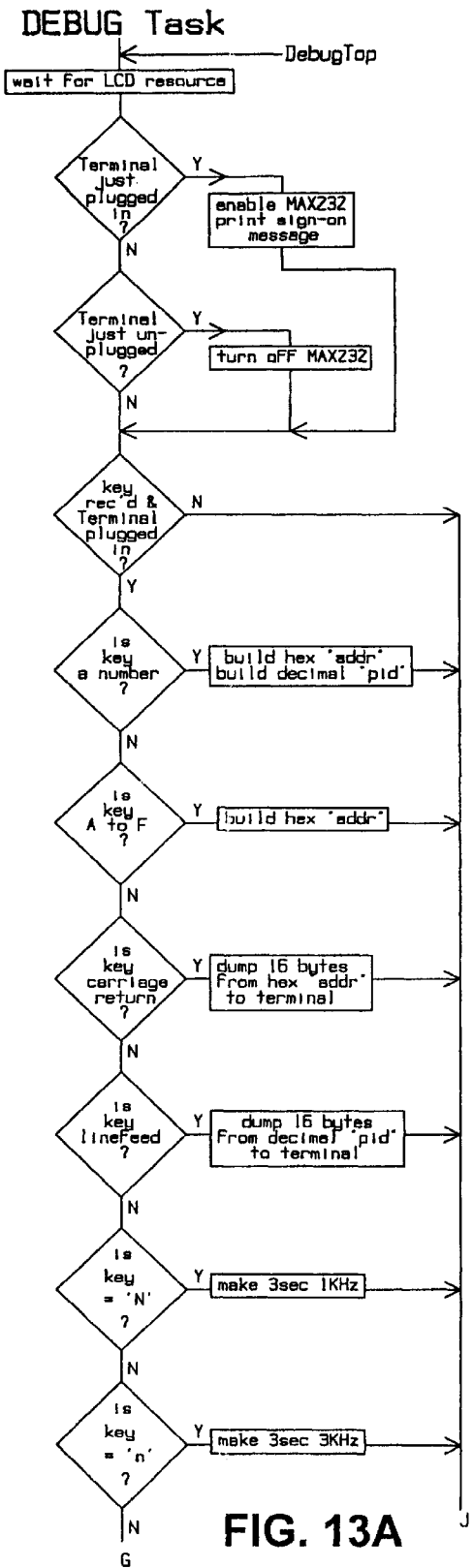
FIGS. 13a and 13b are flow charts showing the sequence of operations internal to the remote patient monitoring device during the DEBUG, PERIOD, and PACER INHIBIT Tasks.
Figure 13A:
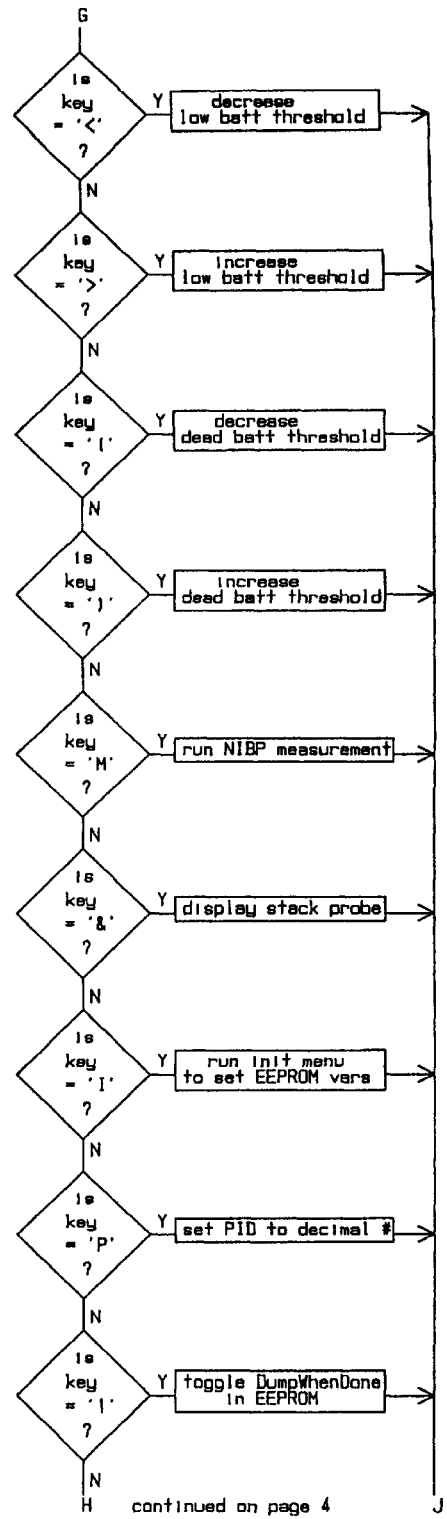
Figure 13B:
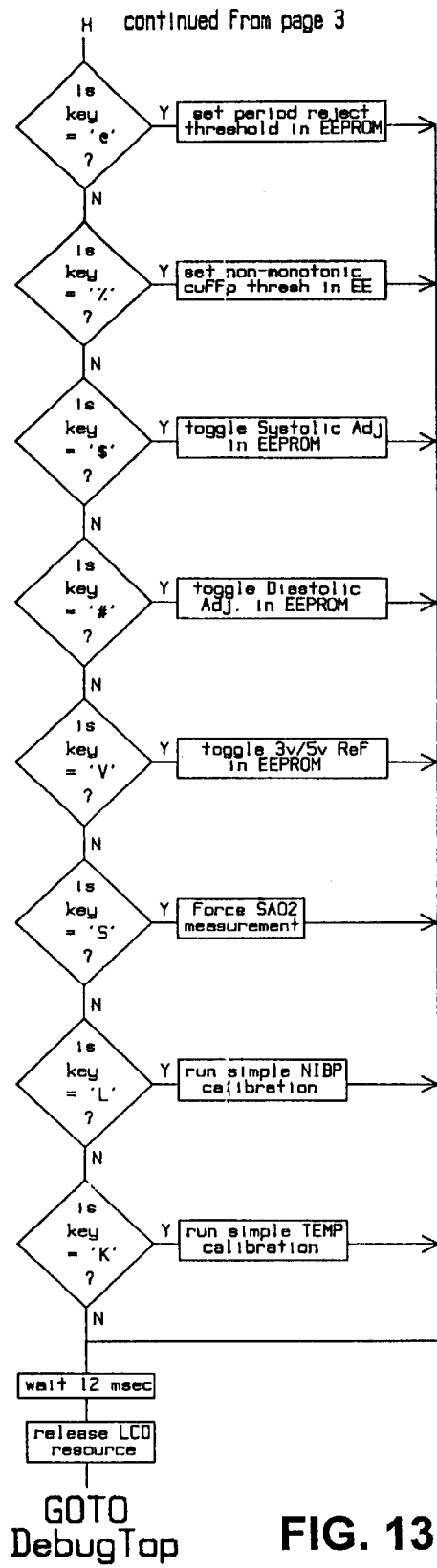
Figure 13B:
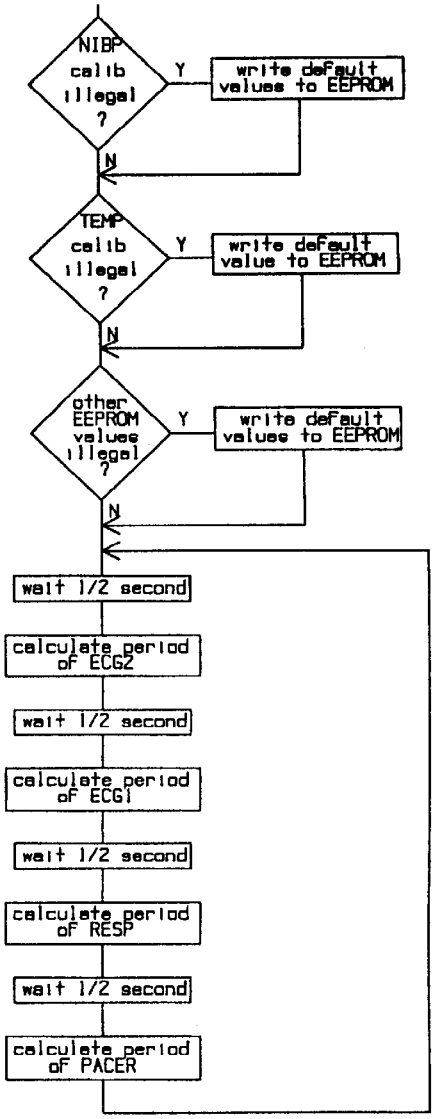
Figure 13B:
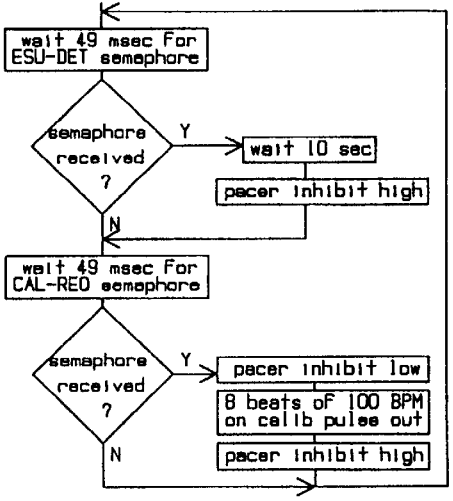

The Debug Task is shown on FIGS. 13a and 13b. The Debug Task primarily handles communications between the user and the device 10 through port 16. This allows device 10 to be calibrated, tested, and debugged, and further allows for external setting of the patient identification number. The Debug Task can run only when display 42 is available and no other higher priority tasks are ready to run.

When the Debug Task detects that a terminal has been connected at port 16 (by detecting the DTR signal) it turns on serial port switch 36 (FIG. 2), turns on serial data I/O driver 35 and prints a prompt to the connected terminal. When the task detects that the terminal has been disconnected from port 16, it turns off driver 35. Priority of the Debug Task is forty.

Pulse Oximetry (SpO₂) Task

The SpO₂ Task (not shown) performs the pulse oximetry measurement whenever it is directed by the SpO₂ Schedule Task, which sets the SpO₂ semaphore. This task powers up pulse oximetry transducer 39 through solid state relay unit 37 and waits for packets of data from it. If no packets are received, the task gives up, removes power from transducer 39, and reports a failure. If the received packets represent good data, the task removes power from transducer 39 and reports. Priority is 28.

Period Task

The Period Task is illustrated on FIG. 13b. The purpose of the Period Task is to determine, at one-half second intervals, the heart rate, respiration rate, and the period of a pacemaker pulse. Priority is 5.

Pacer Inhibit Task

The purpose of the Pacer Inhibit Task, shown on FIG. 13b, is to disable the ECG wave form during detection of a pacemaker pulse by pacemaker pulse detector 67 (PACER DET on FIG. 7). Thus, when the Push Button Poll Task (FIG. 14a) sets the ESU Detect semaphore, this task sets the pacer inhibit signal (PACER INH on FIG. 7) low for four seconds and then returns it to high. The priority of the Pacer Inhibit Task is 36.

Push Button Poll Task

Figure 14:
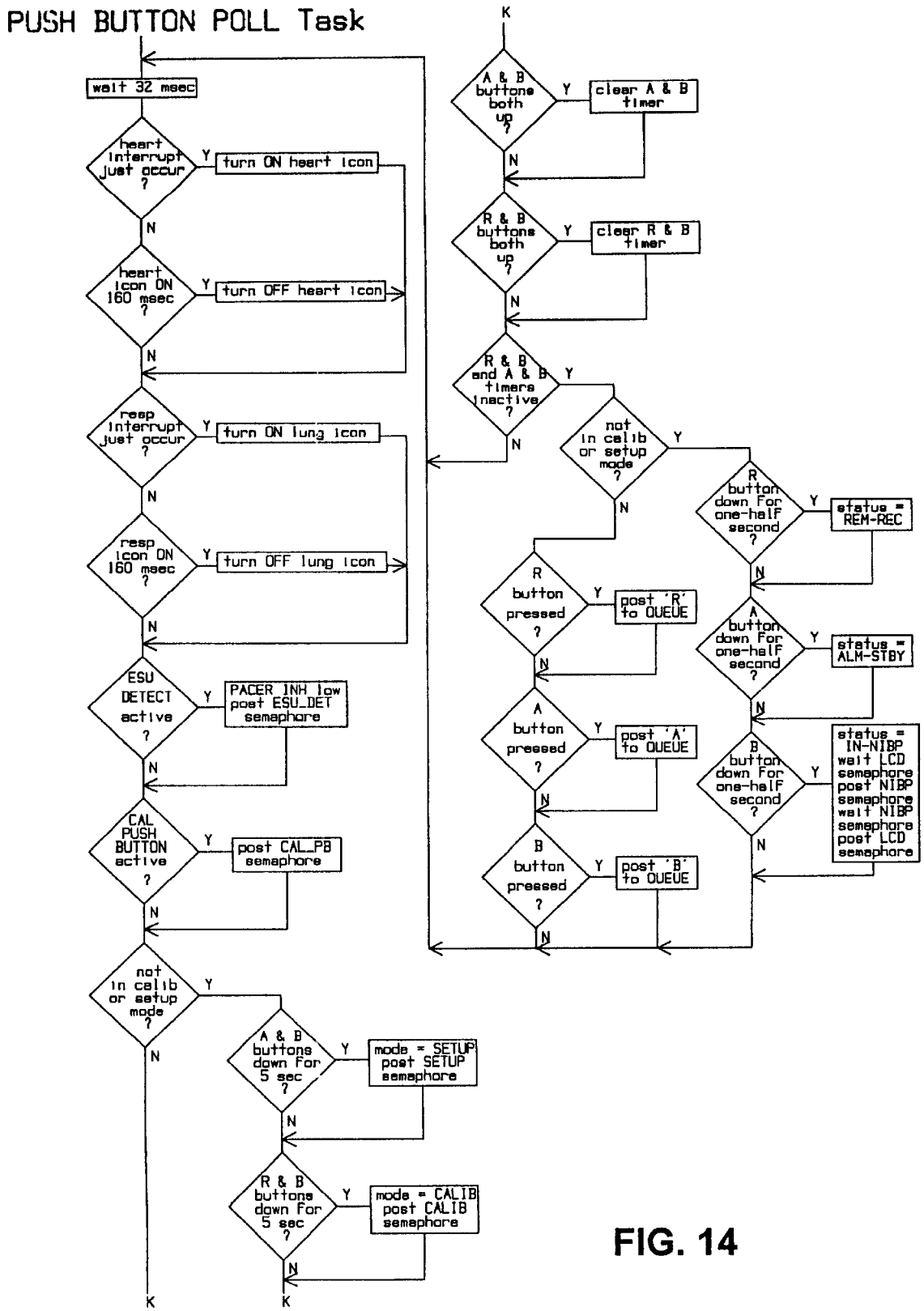
FIG. 14 are flow charts showing the internal sequential operations of the remote patient monitoring device during the PUSH BUTTON POLL Task.

The Push Button Poll Task, shown on FIG. 14, polls front panel switches 41a–d and other slow inputs of device 10 every thirty-two milliseconds. If noise detector circuit 62 generates a noise detect signal (ESU D.out on FIG. 7), the Push Button Poll Task sets the ESU Detect semaphore.

If remote record front panel switch 41b is pressed for one-half second, a remote record command signal is generated by processor 14 in the status word for device 10. When received by the central monitoring station, the remote record command causes activation vital sign recording devices. If alarm/standby switch 41a is pressed, an alarm standby signal is generated, placing device 10 is a standby mode. If the NIBP STAT switch 41d is activated, this task sets the BP semaphore. This task also turns off the heart and/or lung displays icon for one-quarter second after they have been turned on by the ECG or respiration interrupt routines. The priority of the Push Button Pull Task is 34.

Set Up Task

Figure 15A:
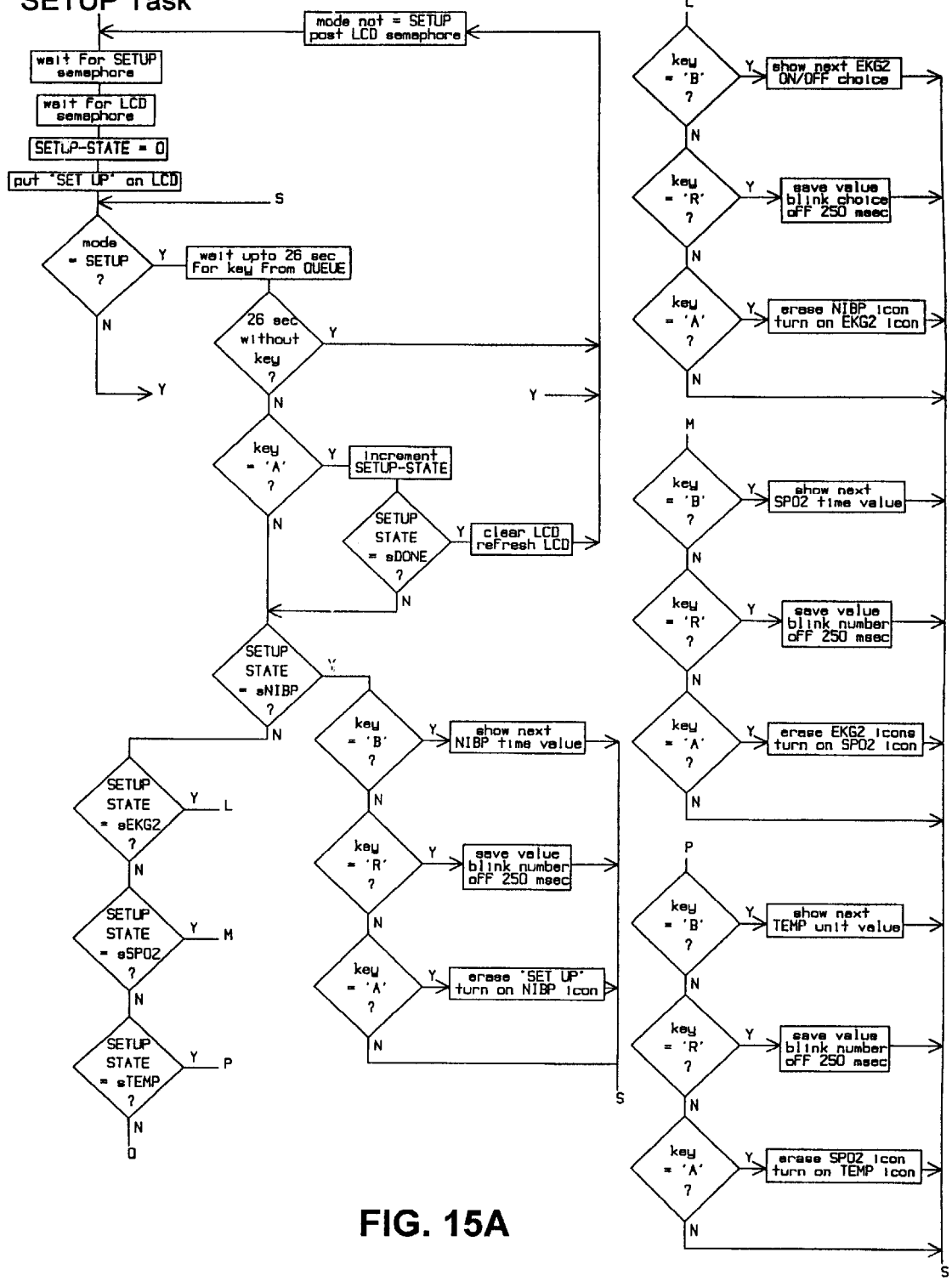
FIGS. 15b and 15b are flow charts showing the sequence of operations internal to the remote patient monitoring device during the SET UP and PIEZO Tasks.
Figure 15B:
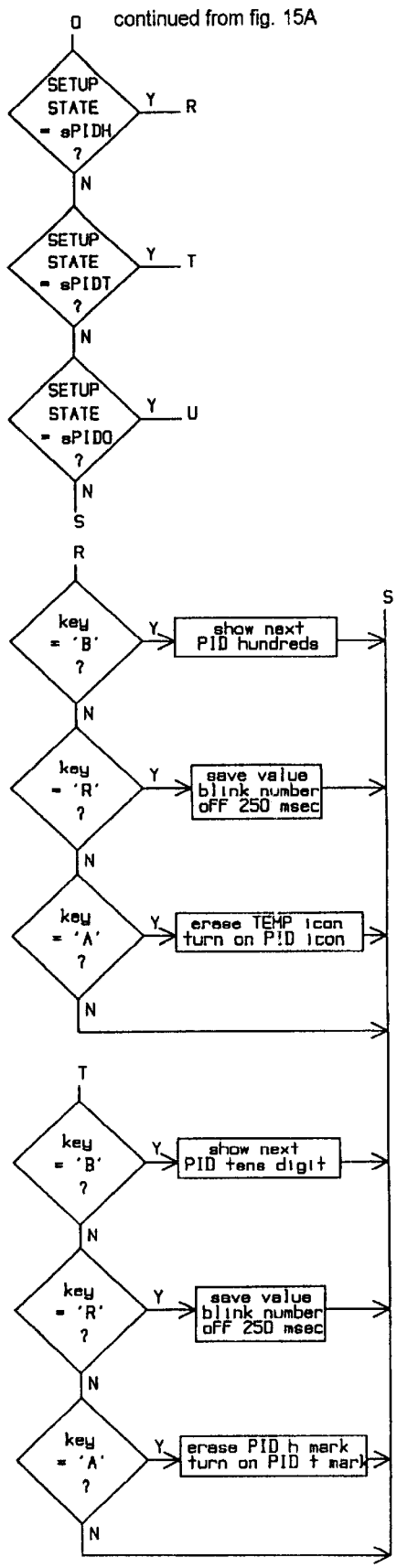
Figure 15B:
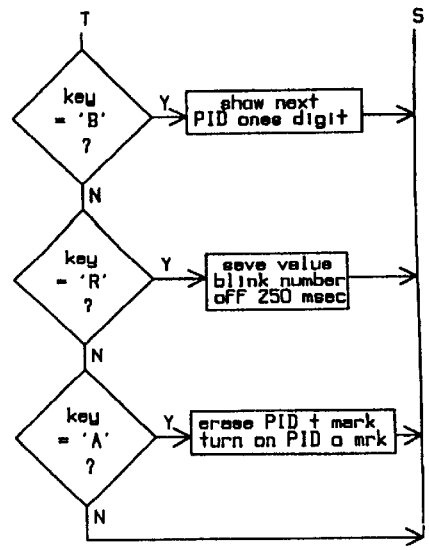
Figure 15B:
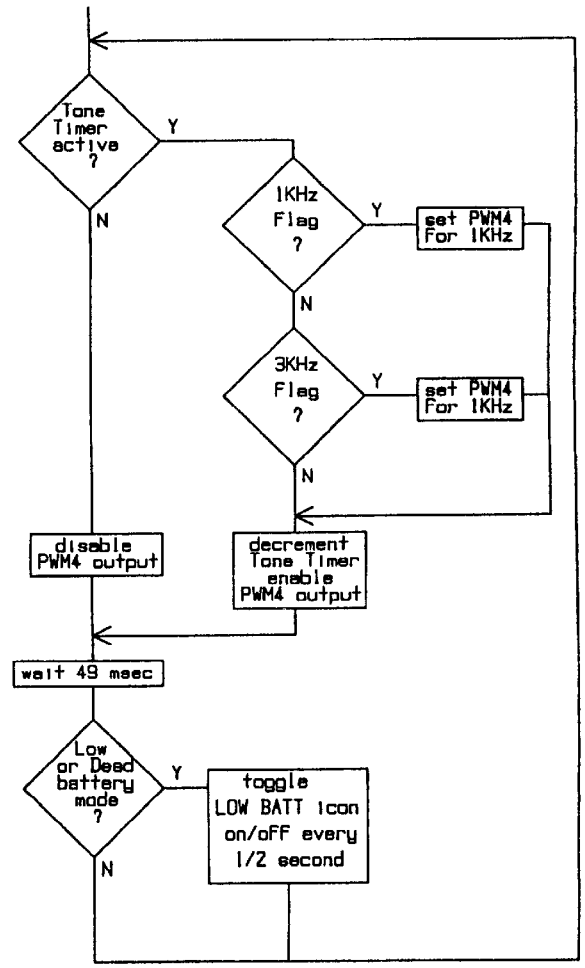

The Set Up Task is shown on FIGS. 15a and 15b. The function of the Set Up Task is to allow the user of device 10 to establish the duty cycle for reading blood pressure and pulse oximetry, i.e., how many readings per hour. The preferred duty cycle is provided by the user through debug/program port 16, with the pulse oximetry and blood pressure intervals downloaded into program memory unit 28. The interval for taking temperature measurements and temperature scale (Fahrenheit or Centigrade) can also be established during the set up task.

Piezo Task

If device 10 includes a sound transducer, such as a piezoelectric device, the Piezo Task, shown on FIG. 15b, determines whether the tone is active and the frequency of the beeps which are emitted.

Calibration Task

Figure 16:
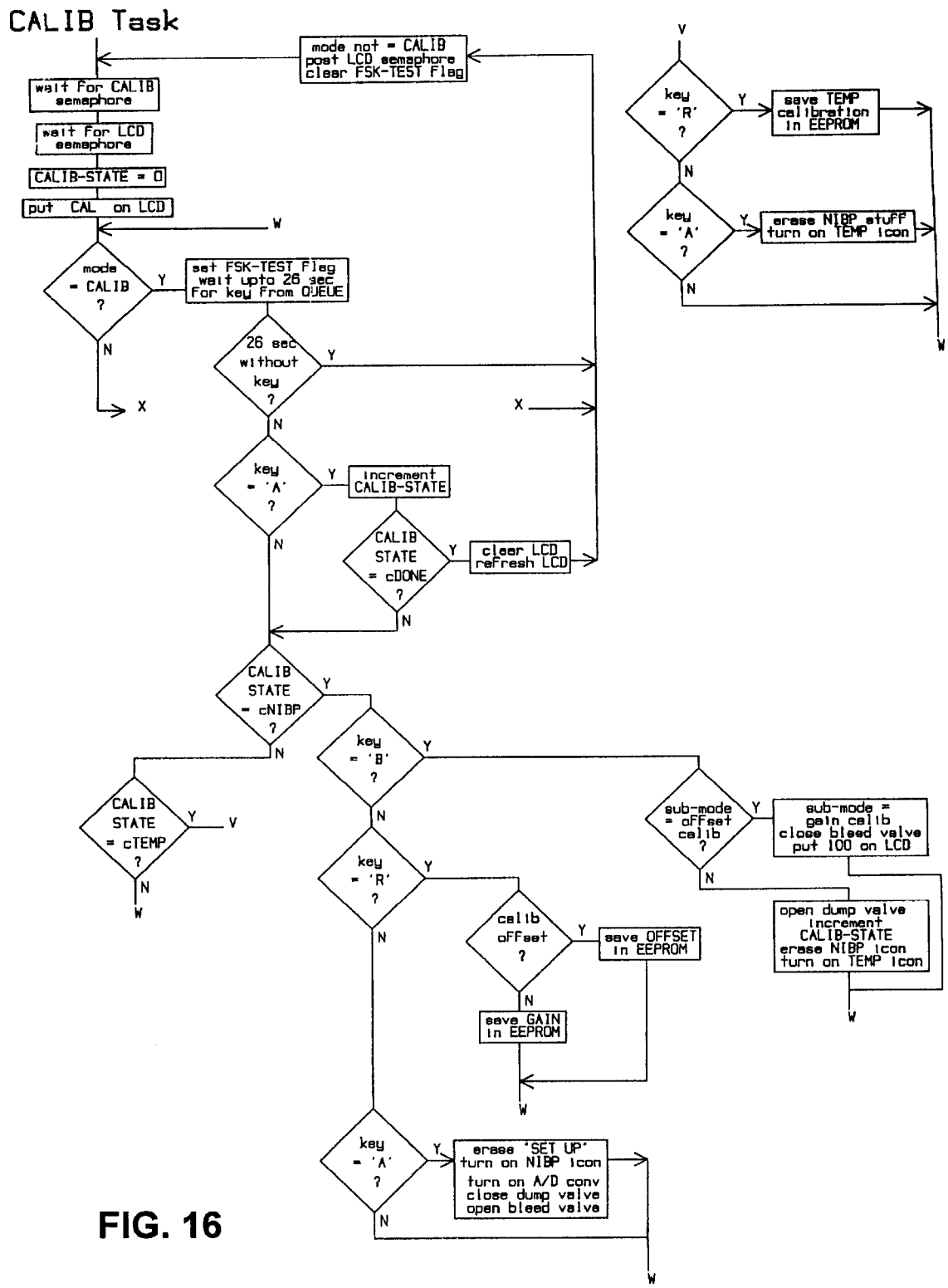
FIG. 16 is a flow chart showing the sequence of events internal to the remote patient monitoring device during the CALIB Task.

The Calibration Task, illustrated on FIG. 16, allows the user to calibrate the blood pressure and temperature 10 circuitry of device 10 by operating front panel switches 41a–d.

Thus, although there have been described particular embodiments of the present invention of a new and useful remote patient monitoring device, it is not intended that such references be construed as limitations upon the scope of this invention except as set forth in the following claims. Further, although there have been described certain dimensions and operational parameters used in the preferred embodiment, it is not intended that such dimensions and operating parameters be construed as limitations upon the scope of this invention except as set forth in the following claims.

What is claimed is:

1. A portable device for monitoring vital signs of a patient, the device comprising:

a. a housing having a thickness, width, and length, and the device being powered by a battery, whereby the housing is portable and sufficiently small such that the device is worn by the patient;

b. transducer interface means for receiving and processing raw vital sign data from a plurality of vital sign transducers associated with a patient, and for generating processed vital sign data, the receiving and processing of vital sign data occurring on a continuous real time basis while the device is worn by the patient;

c. wireless transmitter means for transmitting the processed vital sign data to a remote monitoring station on a continuous real time basis while the device is worn by the patient;

d. said transducer interface means and said transmitter means mounted internal to said housing;

e. display means for displaying said processed vital sign data, said display means mounted on a front panel of said housing;

f. switch means for a user of the device to manually enter data and commands into the device, the switch means mounted on the front panel of the housing and operatively connected to the transducer interface means;

g. said transducer interface means comprising a first channel ECG interface circuit means for receiving and processing ECG data from a first ECG transducer, a blood pressure interface circuit means for receiving and processing blood pressure data from a blood pressure transducer, a pulse oximetry interface circuit means for receiving and processing pulse oximetry data from a pulse oximetry transducer, a respiration interface circuit means for receiving and processing respiration data from a respiration transducer, and a temperature interface circuit means for receiving and processing temperature data from a temperature transducer;

h. said transducer interface means further comprising a second channel ECG interface circuit means for receiving and processing ECG data from a second ECG transducer;

i. said first channel ECG interface circuit means comprising pacer detect means for detecting a pacemaker pulse from the first channel ECG transducers;

j. said transmitter means including modulator means for simultaneously transmitting the processed vital sign data in digital and analog formats;

k. said display means including means for simultaneous display of the processed vital sign data associated with each of the first and second channel ECG, blood pressure, pulse oximetry, respiration, and temperature transducer interface circuit means;

l. blood pressure transducer control means for activating the blood pressure transducer;

m. pulse oximetry transducer control means for activating the pulse oximetry transducer.

n. logic control means associated with said blood pressure transducer control means and said pulse oximetry transducer control means for periodically activating the blood pressure and pulse oximetry transducers at predetermined vital sign sampling intervals;

o. a programming port operatively associated with said logic control means;

p. remote control signaling means for transmitting a recording command signal from the device to activate a vital sign recording unit at the remote monitoring station; and q. said logic control means comprising a serial data input and a port switch means to switch said port between said programming port and said pulse oximetry interface circuit means.

2. A remote patient monitoring device for use with a plurality of external vital sign transducers, the device comprising:

a. a processor unit, said processor unit including data output means for communicating vital sign is data on a continuous real time basis external to said processor unit;

b. a display unit operatively linked to said processor data output means;

c. at least one switch operatively linked to said processor unit;

d. a blood pressure interface circuit, a pulse oximetry interface circuit, a temperature interface circuit, an ECG interface circuit, and a respiration interface circuit, each of said interface circuits operatively connected to said processor unit;

e. transmitter means for transmitting an RF signal to a remote monitoring location;

f. said transmitter means including a modulation means for modulating said RF signal, said modulation means operatively connected to said data output means of said processor unit whereby the vital sign data is communicated to the remote monitoring location in conjunction with the RF signal on a continuous real time basis; and g. a device housing, including a front panel, said display unit and said switch mounted on said front panel, and said processor unit, each of said interface circuits, and said transmitter means being internal to said housing.

* * * * *